United States Patent
Donovan et al.

(10) Patent No.: US 12,427,049 B2
(45) Date of Patent: *Sep. 30, 2025

(54) OSTOMY WAFERS INCORPORATING ADHESIVES, OSTOMY DEVICES INCLUDING THE SAME, AND METHODS OF APPLYING OSTOMY WAFERS AND OSTOMY DEVICES

(71) Applicant: CONVATEC TECHNOLOGIES INC., Las Vegas, NV (US)

(72) Inventors: Emily Donovan, Deeside (GB); Garry Storey, Deeside (GB); Wayne Bonnefin, Deeside (GB); Roxanna Woodward, Deeside (GB); Stephen Desmond, Deeside (GB); Lisa Price, Deeside (GB); Clive Wilson, Deeside (GB); James Glover, Deeside (GB)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 290 days.

This patent is subject to a terminal disclaimer.

(21) Appl. No.: 18/114,966

(22) Filed: Feb. 27, 2023

(65) Prior Publication Data

US 2023/0201023 A1 Jun. 29, 2023

Related U.S. Application Data

(63) Continuation of application No. 16/859,491, filed on Apr. 27, 2020, now Pat. No. 11,590,017.

(Continued)

(51) Int. Cl.
*A61F 5/448* (2006.01)
*A61F 5/44* (2006.01)
*A61F 5/443* (2006.01)

(52) U.S. Cl.
CPC .............. *A61F 5/448* (2013.01); *A61F 5/443* (2013.01); *A61F 2005/4483* (2013.01)

(58) Field of Classification Search
CPC ... A61F 5/448; A61F 5/443; A61F 2005/4483
See application file for complete search history.

(56) References Cited

U.S. PATENT DOCUMENTS 4,834,731 A * 5/1989 Nowak .................. A61F 5/448
604/339
6,520,943 B1 * 2/2003 Wagner .................. A61F 5/443
604/338

(Continued)

FOREIGN PATENT DOCUMENTS

EP 0415282 A1 3/1991
EP 3643224 A1 4/2020

(Continued)

OTHER PUBLICATIONS

US 10,806,622 B2, 10/2020, Hansen et al. (withdrawn)

(Continued)

*Primary Examiner* — Guy K Townsend
(74) *Attorney, Agent, or Firm* — TAFT STETTINIUS HOLLISTER LLP; Ryan O. White; Derek Lavender

(57) ABSTRACT

Ostomy wafers, ostomy devices incorporating ostomy wafers, and methods of applying ostomy wafers and ostomy devices are disclosed herein. An ostomy wafer may include an external layer and a convex surface coupled to the external layer. An ostomy device may include an ostomy pouch and an ostomy wafer coupled to the ostomy pouch that includes an external layer and a convex surface coupled to the external layer.

20 Claims, 7 Drawing Sheets

Related U.S. Application Data

(60) Provisional application No. 62/838,895, filed on Apr. 25, 2019.

(56) References Cited

U.S. PATENT DOCUMENTS

| | | | |
|---|---|---|---|
| 8,449,513 B2* | 5/2013 | Abrams | A61F 5/449 604/342 |
| 8,979,811 B2 | 3/2015 | Keleny et al. | |
| 9,968,480 B2 | 5/2018 | Nyberg | |
| 9,999,537 B2* | 6/2018 | Ekfeldt | A61F 5/445 |
| 10,278,857 B2 | 5/2019 | Hansen et al. | |
| D862,691 S | 10/2019 | Fenton | |
| 10,434,015 B2 | 10/2019 | Taylor et al. | |
| 10,434,309 B2 | 10/2019 | Forsell | |
| 10,449,081 B2 | 10/2019 | Lee | |
| 10,449,082 B2 | 10/2019 | Johnsen | |
| 10,463,527 B2 | 11/2019 | Gallant et al. | |
| 10,470,917 B2 | 11/2019 | Chang | |
| 10,470,918 B2 | 11/2019 | Bendix | |
| 10,471,173 B2 | 11/2019 | Misawa | |
| 10,478,328 B2 | 11/2019 | Guidry et al. | |
| 10,478,329 B2 | 11/2019 | Oberholtzer et al. | |
| 10,478,330 B2 | 11/2019 | Wiltshire et al. | |
| 10,500,084 B2 | 12/2019 | Hansen et al. | |
| 10,500,315 B2 | 12/2019 | Chang et al. | |
| 10,507,318 B2 | 12/2019 | Jin et al. | |
| 10,512,562 B2 | 12/2019 | Kavanagh et al. | |
| 10,517,754 B2* | 12/2019 | Praame | A61F 5/443 |
| 10,524,953 B2 | 1/2020 | Hanuka et al. | |
| 10,531,978 B2 | 1/2020 | Haas et al. | |
| 10,537,461 B2 | 1/2020 | Hanuka et al. | |
| 10,537,462 B1 | 1/2020 | Hatchett et al. | |
| 10,583,029 B2 | 3/2020 | Chang | |
| 10,588,773 B2 | 3/2020 | Tsai et al. | |
| 10,610,402 B1 | 4/2020 | Idowu et al. | |
| 10,617,554 B2 | 4/2020 | Luce | |
| 10,617,555 B2 | 4/2020 | James et al. | |
| 10,646,370 B2 | 5/2020 | Keleny et al. | |
| 10,653,551 B2 | 5/2020 | Apolinario et al. | |
| 10,660,784 B2 | 5/2020 | Nishtala et al. | |
| 10,660,785 B2 | 5/2020 | Kaufman et al. | |
| 10,660,786 B2* | 5/2020 | Obst | A61M 1/916 |
| 10,729,806 B2 | 8/2020 | Bingol et al. | |
| 10,736,769 B2 | 8/2020 | Grove Sund et al. | |
| 10,744,224 B2 | 8/2020 | Israelson et al. | |
| 10,758,398 B2 | 9/2020 | Murthy Aravalli et al. | |
| 10,779,986 B2 | 9/2020 | Cox | |
| 10,799,385 B2 | 10/2020 | Hansen et al. | |
| 10,813,786 B2 | 10/2020 | Lysgaard | |
| 10,813,787 B2 | 10/2020 | Dinakara et al. | |
| 11,076,978 B2 | 8/2021 | Nguyen-Demary et al. | |
| 11,076,979 B2 | 8/2021 | Fattman et al. | |
| 11,083,617 B2 | 8/2021 | Larsen | |
| 11,166,838 B2 | 11/2021 | Cline et al. | |
| 11,246,739 B2 | 2/2022 | Ekfeldt et al. | |
| 11,304,842 B2 | 4/2022 | Becker et al. | |
| 11,590,017 B2* | 2/2023 | Donovan | A61F 5/443 |
| 11,638,658 B2* | 5/2023 | Donovan | A61F 5/448 604/344 |
| 11,679,020 B2* | 6/2023 | Donovan | A61F 5/445 604/336 |
| 11,737,906 B2 | 8/2023 | Jones | |
| 12,193,964 B2* | 1/2025 | Donovan | A61F 5/443 |
| 2004/0006320 A1* | 1/2004 | Buglino | A61F 5/443 604/344 |
| 2004/0193123 A1* | 9/2004 | Fenton | A61F 5/448 604/344 |
| 2004/0267216 A1 | 12/2004 | Udayakumar et al. | |
| 2006/0058576 A1 | 3/2006 | Davies et al. | |
| 2010/0168693 A1* | 7/2010 | Edvardsen | A61F 5/451 604/355 |
| 2010/0174253 A1 | 7/2010 | Cline et al. | |
| 2010/0324511 A1* | 12/2010 | Dove | A61F 5/445 604/338 |
| 2011/0218507 A1 | 9/2011 | Andersen et al. | |
| 2012/0041400 A1 | 2/2012 | Christensen | |
| 2012/0109086 A1 | 5/2012 | Tsai | |
| 2012/0136324 A1 | 5/2012 | Hanuka et al. | |
| 2012/0179124 A1 | 7/2012 | Nguyen-Demary et al. | |
| 2012/0232506 A1* | 9/2012 | Todd | A61F 5/445 604/339 |
| 2013/0072886 A1 | 3/2013 | Schertiger et al. | |
| 2013/0226063 A1 | 8/2013 | Taylor et al. | |
| 2014/0207094 A1 | 7/2014 | Chang | |
| 2014/0221950 A1 | 8/2014 | Chang et al. | |
| 2014/0276501 A1 | 9/2014 | Cisko | |
| 2014/0288517 A1 | 9/2014 | Tsai et al. | |
| 2014/0316360 A1* | 10/2014 | Ekfeldt | A61F 5/445 604/338 |
| 2015/0133881 A1 | 5/2015 | Freiding | |
| 2015/0209172 A1 | 7/2015 | Richmann et al. | |
| 2015/0359656 A1* | 12/2015 | Hansen | A61F 5/443 604/344 |
| 2016/0151198 A1 | 6/2016 | Frampton et al. | |
| 2016/0193003 A1 | 7/2016 | Todd et al. | |
| 2016/0206469 A1 | 7/2016 | Prezelin | |
| 2017/0007440 A1 | 1/2017 | Moavenian | |
| 2017/0065451 A1 | 3/2017 | Brandt et al. | |
| 2017/0143535 A1* | 5/2017 | Praame | A61F 5/443 |
| 2017/0209295 A1 | 7/2017 | Smith et al. | |
| 2017/0209296 A1 | 7/2017 | Cailleteau | |
| 2018/0064572 A1 | 3/2018 | Wiltshire | |
| 2018/0235801 A1* | 8/2018 | Oellgaard | A61F 5/443 |
| 2018/0236207 A1 | 8/2018 | Shankarsetty | |
| 2018/0303655 A1 | 10/2018 | Glithero et al. | |
| 2018/0311066 A1 | 11/2018 | Hansen et al. | |
| 2018/0325718 A1* | 11/2018 | Ekfeldt | A61F 5/445 |
| 2018/0344506 A1 | 12/2018 | Larsen | |
| 2018/0360644 A1 | 12/2018 | Ponce | |
| 2018/0369474 A1 | 12/2018 | Falleboe et al. | |
| 2019/0015241 A1 | 1/2019 | Lin et al. | |
| 2019/0029868 A1 | 1/2019 | Grum-Schwensen et al. | |
| 2019/0110919 A1 | 4/2019 | Beckers et al. | |
| 2019/0117824 A1 | 4/2019 | Hansen et al. | |
| 2019/0247549 A1 | 8/2019 | Nielsen | |
| 2019/0321213 A1 | 10/2019 | Morrison, Sr. | |
| 2019/0328571 A1 | 10/2019 | Adachi | |
| 2019/0328572 A1 | 10/2019 | Weinberg et al. | |
| 2019/0358076 A1 | 11/2019 | Blatt | |
| 2019/0365560 A1 | 12/2019 | Timms et al. | |
| 2019/0374372 A1 | 12/2019 | Seres et al. | |
| 2019/0380860 A1 | 12/2019 | Eggert et al. | |
| 2019/0380861 A1 | 12/2019 | Nordquist et al. | |
| 2019/0380882 A1 | 12/2019 | Taylor et al. | |
| 2020/0000624 A1 | 1/2020 | Gibbons et al. | |
| 2020/0015996 A1* | 1/2020 | Schertiger | A61F 5/445 |
| 2020/0030134 A1 | 1/2020 | Hopper | |
| 2020/0038226 A1 | 2/2020 | Botten et al. | |
| 2020/0038227 A1 | 2/2020 | Makar, Jr. | |
| 2020/0038228 A1 | 2/2020 | Aravalli et al. | |
| 2020/0038229 A1 | 2/2020 | Aravalli | |
| 2020/0046541 A1 | 2/2020 | Sund et al. | |
| 2020/0046542 A1 | 2/2020 | Guidry et al. | |
| 2020/0046543 A1 | 2/2020 | Scalise et al. | |
| 2020/0054476 A1 | 2/2020 | Miller | |
| 2020/0054478 A1 | 2/2020 | Forsell | |
| 2020/0060863 A1 | 2/2020 | Sund et al. | |
| 2020/0061282 A1 | 2/2020 | Hvid et al. | |
| 2020/0069455 A1 | 3/2020 | Oberholtzer et al. | |
| 2020/0069529 A1 | 3/2020 | Starnes et al. | |
| 2020/0078206 A1 | 3/2020 | Chiladakis | |
| 2020/0085608 A1 | 3/2020 | Hrushka et al. | |
| 2020/0093633 A1 | 3/2020 | Blumrosen et al. | |
| 2020/0100931 A1 | 4/2020 | Schoess et al. | |
| 2020/0100946 A1 | 4/2020 | Wohlgemuth et al. | |
| 2020/0121490 A1 | 4/2020 | Woodward et al. | |
| 2020/0138618 A1 | 5/2020 | Roszkowiak et al. | |
| 2020/0138619 A1 | 5/2020 | Cisko, Jr. et al. | |
| 2020/0146944 A1 | 5/2020 | Moulton et al. | |
| 2020/0155338 A1 | 5/2020 | Meteer | |
| 2020/0163792 A1 | 5/2020 | Schertiger | |
| 2020/0164196 A1 | 5/2020 | Jin et al. | |
| 2020/0188160 A1 | 6/2020 | Udayakumar | |

(56) References Cited

U.S. PATENT DOCUMENTS

| | | |
|---|---|---|
| 2020/0188161 A1 | 6/2020 | Seres et al. |
| 2020/0188162 A1 | 6/2020 | Menifee |
| 2020/0197213 A1 | 6/2020 | Frampton-Vallance et al. |
| 2020/0214371 A1 | 7/2020 | Apelt |
| 2020/0214872 A1 | 7/2020 | Tretheway et al. |
| 2020/0214873 A1 | 7/2020 | Tretheway et al. |
| 2020/0214875 A1 | 7/2020 | Tretheway et al. |
| 2020/0229962 A1 | 7/2020 | Torstensen et al. |
| 2020/0237550 A1 | 7/2020 | Hussey et al. |
| 2020/0246173 A1 | 8/2020 | Schertiger et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 * | 8/2020 | Hansen .................... A61F 5/445 |
| 2020/0246178 A1 | 8/2020 | O'Hamill et al. |
| 2020/0253633 A1 | 8/2020 | Obst et al. |
| 2020/0253777 A1 | 8/2020 | Jones |
| 2020/0261254 A1 | 8/2020 | Williams et al. |
| 2020/0276044 A1 | 9/2020 | Tretheway et al. |
| 2020/0276045 A1 | 9/2020 | Bendavit |
| 2020/0281758 A1 | 9/2020 | Tan |
| 2020/0281759 A1 | 9/2020 | Lu |
| 2020/0281761 A1 | 9/2020 | Tretheway et al. |
| 2020/0289307 A1 | 9/2020 | Tretheway et al. |
| 2020/0289308 A1 | 9/2020 | Tretheway et al. |
| 2020/0297524 A1 * | 9/2020 | Hunt ........................ A61F 5/448 |
| 2020/0306073 A1 | 10/2020 | Olsen et al. |
| 2020/0306074 A1 | 10/2020 | Speiermann et al. |
| 2020/0330258 A1 | 10/2020 | Hansen et al. |
| 2020/0330259 A1 | 10/2020 | Sund et al. |
| 2020/0330260 A1 | 10/2020 | Hansen et al. |
| 2020/0337879 A1 * | 10/2020 | Donovan ................. A61F 5/445 |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0337884 A1 * | 10/2020 | Donovan ................. A61F 5/448 |
| 2020/0337885 A1 * | 10/2020 | Donovan ................. A61F 5/448 |
| 2020/0338230 A1 | 10/2020 | Israelson et al. |
| 2021/0244497 A1 | 8/2021 | Taweh |
| 2022/0054296 A1 | 2/2022 | Allen |
| 2022/0054297 A1 | 2/2022 | Cline et al. |
| 2022/0062024 A1 | 3/2022 | Allen |
| 2023/0201023 A1 * | 6/2023 | Donovan ................. A61F 5/448 604/344 |
| 2023/0201024 A1 * | 6/2023 | Donovan ................. A61F 5/448 604/344 |
| 2023/0255814 A1 * | 8/2023 | Donovan ................. A61F 5/443 604/344 |
| 2023/0263652 A1 * | 8/2023 | Donovan ................. A61F 5/443 604/336 |
| 2024/0000601 A1 | 1/2024 | Jones, Jr. |

FOREIGN PATENT DOCUMENTS

| | | | |
|---|---|---|---|
| EP | 3897479 A1 | 10/2021 | |
| EP | 3897813 A1 | 10/2021 | |
| EP | 3955864 A1 | 2/2022 | |
| EP | 3998052 A1 | 5/2022 | |
| EP | 3725274 B1 | 3/2024 | |
| GB | 2534012 A | 7/2016 | |
| GB | 2544180 A | 5/2017 | |
| GB | 2548673 A | 9/2017 | |
| GB | 2550936 A | 12/2017 | |
| GB | 2570526 A | 7/2019 | |
| GB | 2575687 A | 1/2020 | |
| GB | 2571835 B | 2/2020 | |
| GB | 2579873 B | 8/2023 | |
| WO | 03075808 A1 | 9/2003 | |
| WO | 2015110544 A1 | 7/2015 | |
| WO | 2015138190 A1 | 9/2015 | |
| WO | 2015148035 A1 | 10/2015 | |
| WO | WO-2018054442 A1 * | 3/2018 | ............ A61F 5/44 |
| WO | 2018188706 A1 | 10/2018 | |
| WO | 2018188707 A1 | 10/2018 | |
| WO | 2019058126 A1 | 3/2019 | |
| WO | 2019058127 A1 | 3/2019 | |
| WO | 2019091526 A1 | 5/2019 | |
| WO | 2019091527 A1 | 5/2019 | |
| WO | 2019091528 A1 | 5/2019 | |
| WO | 2019091529 A1 | 5/2019 | |
| WO | 2019091532 A1 | 5/2019 | |
| WO | 2019099662 A1 | 5/2019 | |
| WO | 2019120424 A1 | 6/2019 | |
| WO | 2019120429 A1 | 6/2019 | |
| WO | 2019120430 A1 | 6/2019 | |
| WO | 2019120432 A1 | 6/2019 | |
| WO | 2019120433 A1 | 6/2019 | |
| WO | 2019120434 A1 | 6/2019 | |
| WO | 2019120437 A1 | 6/2019 | |
| WO | 2019120438 A1 | 6/2019 | |
| WO | 2019120439 A1 | 6/2019 | |
| WO | 2019120442 A1 | 6/2019 | |
| WO | 2019120443 A1 | 6/2019 | |
| WO | 2019120444 A1 | 6/2019 | |
| WO | 2019120446 A1 | 6/2019 | |
| WO | 2019120448 A1 | 6/2019 | |
| WO | 2019120449 A1 | 6/2019 | |
| WO | 2019120450 A1 | 6/2019 | |
| WO | 2019120451 A1 | 6/2019 | |
| WO | 2019120452 A1 | 6/2019 | |
| WO | 2019120458 A1 | 6/2019 | |
| WO | 2019197291 A1 | 10/2019 | |
| WO | 2019197971 A1 | 10/2019 | |
| WO | 2019198012 A1 | 10/2019 | |
| WO | 2019221830 A1 | 11/2019 | |
| WO | 2019229267 A2 | 12/2019 | |
| WO | 2019229268 A1 | 12/2019 | |
| WO | 2019242828 A1 | 12/2019 | |
| WO | 2020008470 A1 | 1/2020 | |
| WO | 2020010766 A1 | 1/2020 | |
| WO | 2020014305 A1 | 1/2020 | |
| WO | 2020016471 A1 | 1/2020 | |
| WO | 2020035121 A1 | 2/2020 | |
| WO | 2020044081 A1 | 3/2020 | |
| WO | 2020055998 A1 | 3/2020 | |
| WO | 2020076607 A1 | 4/2020 | |
| WO | 2020076609 A1 | 4/2020 | |
| WO | 2020084282 A1 | 4/2020 | |
| WO | 2020125906 A1 | 6/2020 | |
| WO | 2020125907 A1 | 6/2020 | |
| WO | 2020128456 A1 | 6/2020 | |
| WO | 2020128457 A1 | 6/2020 | |
| WO | 2020156624 A1 | 8/2020 | |
| WO | 2020156625 A1 | 8/2020 | |
| WO | 2020156626 A1 | 8/2020 | |
| WO | 2020169162 A1 | 8/2020 | |
| WO | 2020173534 A1 | 9/2020 | |
| WO | 2020174218 A1 | 9/2020 | |
| WO | 2020174219 A1 | 9/2020 | |
| WO | 2020174220 A1 | 9/2020 | |
| WO | 2020174497 A1 | 9/2020 | |
| WO | 2020182923 A1 | 9/2020 | |
| WO | 2020193943 A1 | 10/2020 | |
| WO | 2020200382 A1 | 10/2020 | |
| WO | 2020201718 A1 | 10/2020 | |
| WO | 2020216426 A1 | 10/2020 | |
| WO | 2020216427 A1 | 10/2020 | |
| WO | 2020216429 A1 | 10/2020 | |
| WO | 2020219153 A1 | 10/2020 | |

OTHER PUBLICATIONS

Chinese Office Action, China National Intellectual Property Administration, Chinese Patent Application No. 202080041050.8, Sep. 6, 2023, 10 pages.

Singaporean Written Opinion; Intellectual Property Office of Singapore; Application No. 11202111670V; Jun. 23, 2023; 6 pages.

International Search Report; International Searching Authority; International Application No. PCT/US2020/030089; Jul. 28, 2020; 3 pages.

(56) References Cited

OTHER PUBLICATIONS

Written Opinion of the International Searching Authority, International Searching Authority; International Application No. PCT/US2020/030089; Jul. 28, 2020; 8 pages.
International Preliminary Report on Patentability; International Searching Authority; International Application No. PCT/US2020/030089; Nov. 4, 2021; 9 pages.
European Search Report; European Patent Office; Application No. 20796176.4; May 12, 2022; 3 pages.
European Examination Report; European Patent Office; European Application No. 20796176.4; May 24, 2022; 5 pages.

\* cited by examiner

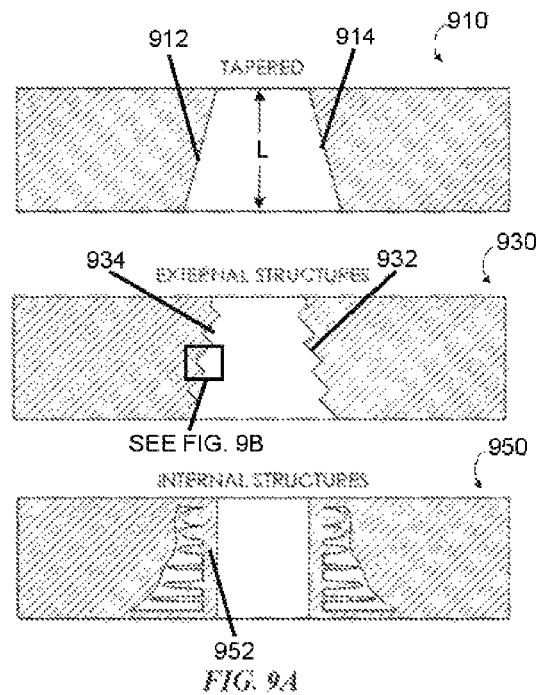
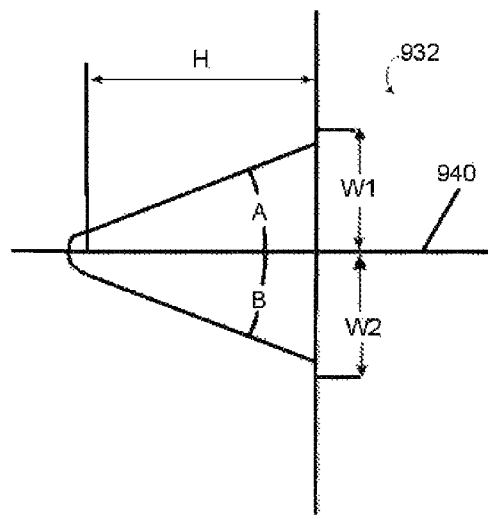

OSTOMY WAFERS INCORPORATING ADHESIVES, OSTOMY DEVICES INCLUDING THE SAME, AND METHODS OF APPLYING OSTOMY WAFERS AND OSTOMY DEVICES

CROSS-REFERENCE TO RELATED APPLICATIONS

This application is a continuation of U.S. application Ser. No. 16/859,491, which was filed on Apr. 27, 2020, and which claims priority to, and the benefit of, U.S. Provisional Patent Application Ser. No. 62/838,895 entitled "Adhesive Ostomy Devices," which was filed on Apr. 25, 2019. The contents of those applications are incorporated herein by reference in their entireties.

FIELD OF THE DISCLOSURE

The present disclosure relates, generally, to ostomy devices, and, more specifically, to ostomy devices adapted for attachment to a patient.

BACKGROUND

Comfort and security may be primary concerns with regards to the attachment of ostomy devices to a person who has undergone a surgical procedure to create an opening in the body (i.e., ostomate). Attachment features incorporated into, coupled to, or otherwise adapted for use with some ostomy devices may lack a desired degree of comfort and/or conformance. Accordingly, ostomy devices that address those shortcomings remain an area of interest.

SUMMARY

The present disclosure may comprise one or more of the following features and combinations thereof.

According to one aspect of the present disclosure, an ostomy wafer may include an external layer and a convex layer. The external layer may have an external opening through which effluent flows in use of the ostomy wafer and a first adhesive that adheres to external skin around a stoma to secure the ostomy wafer to an ostomate. The convex layer may include a stoma channel through which effluent flows, a gap extending radially from the stoma channel, and a second adhesive.

In some embodiments, the ostomy wafer may include a plurality of gaps.

In some embodiments, the ostomy wafer may include a plurality of gaps that are distributed over less than 10% of the radial area of the convex layer.

In some embodiments, the ostomy wafer may include a plurality of gaps that are distributed over more than 10% of the radial area of the convex layer.

In some embodiments, the ostomy wafer may include a plurality of gaps that are distributed over more than 50% of the radial area of the convex layer.

In some embodiments, the ostomy wafer may include a first gap and a second gap that are separated by at least 10% of the radial area of the convex layer.

In some embodiments, the convex layer may include a ridge extending radially in a direction away from the stoma channel toward an outer edge of the convex layer.

In some embodiments, the stoma channel may have a proximal opening that is positioned in a flush or retracted stoma and a distal opening, and a wall of the stoma channel may have a first thickness at the distal opening that is less than a second thickness of the wall at the proximal opening.

In some embodiments, a width of a distal opening of the stoma channel may be greater than a width of a proximal opening of the stoma channel.

In some embodiments, the stoma channel may include a built-in structure.

In some embodiments, the stoma channel may include a built-in structure that is located on an internal surface of the stoma channel.

In some embodiments, the stoma channel may include a built-in structure that is located within a wall of the stoma channel.

In some embodiments, the external layer may include a multilayer adhesive.

In some embodiments, the external layer may include Trilam (SH/DH).

In some embodiments, the convex layer may include a Stomahesive seal.

In some embodiments, a dimension of the convex layer that is parallel with a direction of effluent flow may be greater than 0.5 cm.

In some embodiments, a dimension of the convex layer that is parallel with a direction of effluent flow may be greater than 1.0 cm.

In some embodiments, a dimension of the convex layer that is parallel with a direction of effluent flow may be greater than 2.0 cm.

In some embodiments, at least a portion of the convex layer has a profile selected from a chamfered profile, a cylindrical profile, a curved profile, and combinations thereof.

In some embodiments, at least a portion of the convex layer may include an axially combined profile.

In some embodiments, at least a portion of the convex layer may include a radially combined layer profile.

In some embodiments, the convex layer may include at least two axial segments.

In some embodiments, the convex layer may include at least two radial segments.

In some embodiments, the convex layer may include at least two parallel segments.

In some embodiments, at least a portion of the ostomy wafer may be moldable to the shape or depth of the stoma.

In some embodiments, the ostomy wafer may fit the stoma without being cut.

In some embodiments, the ostomy wafer may be configured for molding to both a first stoma and a second stoma, and the first stoma and the second stoma may differ in shape, size, or depth.

In some embodiments, at least a portion of the convex layer may include a moldable adhesive material.

In some embodiments, the ostomy wafer may include an internal layer that covers at least a portion of a body-facing side of the convex layer, and the internal layer may include a moldable adhesive material.

In some embodiments, a width of the gap may decrease in a distal direction from the stoma channel to an outer edge of the convex layer.

In some embodiments, the gap may be a complete break in the convex layer.

According to another aspect of the present disclosure, an ostomy device may include the ostomy wafer disclosed herein and an ostomy pouch.

In some embodiments, the ostomy wafer may be permanently attached to the ostomy pouch.

In some embodiments, the ostomy wafer and the ostomy pouch may be provided as separate components prior to use.

In some embodiments, the ostomy wafer and the ostomy pouch may be attached and subsequently separated without damage to the ostomy wafer or the ostomy pouch.

According to yet another aspect of the present disclosure, an ostomy wafer may include an external layer and a convex layer coupled to the external layer. The external layer may have an opening to permit the passage of effluent therethrough and a first adhesive to adhere to external skin around a stoma of an ostomate. The convex layer may include a stoma channel sized to at least partially receive the stoma, at least one groove radially spaced from the stoma channel that extends at least partially through the convex layer to facilitate deformation of the convex layer complementary to a shape of the stoma, and a second adhesive to further adhere to the ostomate.

In some embodiments, the at least one groove may include a plurality of grooves spaced circumferentially from one another about the convex layer. At least one of the plurality of grooves may extend through the convex layer to a depth that is less than an entire height of the convex layer. At least one of the plurality of grooves may extend through the convex layer to a depth that is equal to the entire height of the convex layer. Additionally, in some embodiments, the plurality of grooves may be distributed over less than 10% of an entire radial area of the ostomy wafer. The plurality of grooves may include two sets of grooves arranged circumferentially opposite one another about the convex layer. Each of the two sets of grooves may include multiple grooves that extend from a proximal end to a distal end of the convex layer, and the multiple grooves may converge toward the distal end. In some embodiments still, the plurality of grooves may include six grooves that are circumferentially distributed evenly around the convex layer. Each of the six grooves may extend from a proximal end toward a distal end of the convex layer, and a width of each of the six grooves may decrease toward the distal end.

In some embodiments, the convex layer may include at least one protruding ridge that extends radially away from the stoma channel toward an outermost edge of the convex layer. The at least one protruding ridge may include two protruding ridges that each extend radially away from the stoma channel all the way to the outermost edge of the convex layer, and the two protruding ridges may be arranged circumferentially opposite one another about the convex layer. Additionally, in some embodiments, the stoma channel may have a proximal opening sized for receipt in a flush or retracted stoma and a distal opening arranged opposite the proximal opening, and a thickness of a wall of the convex layer at the proximal opening may be greater than a thickness of a wall of the convex layer at the distal opening. A diameter of the distal opening may be greater than a diameter of the proximal opening.

In some embodiments, the stoma channel may include a built-in structure. The built-in structure may be located on an internal surface of the convex layer that defines the stoma channel, and the built-in structure may include a plurality of angled fins that extend toward the stoma and are shaped to mate with the stoma. Additionally, in some embodiments, the built-in structure may be located interiorly of an internal surface of the convex layer that defines the stoma channel.

In some embodiments, the first adhesive may be a multilayer adhesive. Additionally, in some embodiments, the external layer may include Trilam (SH/DH). In some embodiments still, the convex layer may include a Stomahesive seal. In some embodiments yet still, the convex layer may extend in a dimension parallel to a flow of effluent through the ostomy wafer over more than half a centimeter. Further, in some embodiments, at least a portion of the convex layer may be characterized by a profile selected from a chamfered profile, a cylindrical profile, a curved profile, an axially combined profile, a radially combined profile, and combinations thereof.

In some embodiments, the convex layer may be constructed to conform to any one of a number of stomas of different ostomates without modification, and the second adhesive may include a moldable adhesive material. Additionally, in some embodiments, the ostomy wafer may include an internal layer that at least partially covers an exterior of the convex layer that faces the ostomate. The internal layer may include a moldable adhesive material.

According to yet another aspect of the present disclosure still, an ostomy device may include an ostomy pouch and an ostomy wafer coupled to the ostomy pouch. The ostomy wafer may include an external layer and a convex layer coupled to the external layer. The external layer may have an opening to permit the passage of effluent therethrough and a first adhesive to adhere around a stoma of an ostomate. The convex layer may include a stoma channel sized to at least partially receive the stoma, a plurality of grooves radially spaced from the stoma channel that extend at least partially through the convex layer and are spaced circumferentially from one another around the convex layer, and a second adhesive to further adhere to the ostomate.

In some embodiments, at least one of the plurality of grooves may extend through the convex layer to a depth that is equal to the entire height of the convex layer. Additionally, in some embodiments, the plurality of grooves may be distributed over less than 10% of an entire radial area of the ostomy wafer. In some embodiments still, the convex layer may include at least one protruding ridge that extends radially away from the stoma channel toward an outermost edge of the convex layer. In some embodiments yet still, the stoma channel may have a proximal opening sized for receipt in a flush or retracted stoma and a distal opening arranged opposite the proximal opening, and a thickness of a wall of the convex layer at the proximal opening may be greater than a thickness of a wall of the convex layer at the distal opening.

In some embodiments, the stoma channel may include a built-in structure located on an internal surface of the convex layer that defines the stoma channel, and the built-in structure may include a plurality of angled fins that extend toward the stoma and are shaped to mate with the stoma. Additionally, in some embodiments, the stoma channel may include a built-in structure located interiorly of an internal surface of the convex layer that defines the stoma channel. In some embodiments still, the ostomy wafer may include an internal layer that at least partially covers an exterior of the convex layer that faces the ostomate, and the internal layer may have a moldable adhesive material.

According to a further aspect of the present disclosure, a method of applying an ostomy wafer to an ostomate may include positioning a convex layer of the ostomy wafer relative to a stoma of the ostomate, pressing the convex layer against the ostomate to mold the convex layer to the stoma and external skin of the ostomate surrounding the stoma, forming a seal around the stoma with the convex layer, adhering the convex layer to the ostomate with a first adhesive of the convex layer, contacting the convex layer with an external layer of the ostomy wafer, and securing the external layer to the ostomate with a second adhesive of the external layer.

In some embodiments, pressing the convex layer against the ostomate includes deforming the convex layer adjacent to grooves extending at least partway through the convex layer to form a shape of the convex layer that is sized for receipt in a pocket or crease of the external skin of the ostomate. Additionally, in some embodiments, pressing the convex layer against the ostomate may include deforming the convex layer adjacent to grooves extending all the way through the convex layer to form a shape of the convex layer that is sized for receipt in a pocket or crease of the external skin of the ostomate. In some embodiments still, pressing the convex layer against the ostomate includes deforming the convex layer adjacent to grooves extending all the way through the convex layer to accommodate a hernia adjacent to the stoma.

In some embodiments, pressing the convex layer against the ostomate may include filling pockets or creases of the external skin of the ostomate with protruding ridges of the convex layer. Additionally, in some embodiments, pressing the convex layer against the ostomate may include positioning a stoma channel of the convex layer around the stoma and securing the stoma channel to the stoma using a plurality of angled fins formed on an internal surface of the convex layer that defines the stoma channel. In some embodiments still, pressing the convex layer against the ostomate may include positioning a stoma channel of the convex layer around the stoma and securing the stoma channel to the stoma using a plurality of structures located interiorly of an internal surface of the convex layer that defines the stoma channel. In some embodiments yet still, pressing the convex layer against the ostomate may include contacting the ostomate with an internal layer of the ostomy wafer that at least partially covers the convex layer and includes a third adhesive.

These and other features of the present disclosure will become more apparent from the following description of the illustrative embodiments.

BRIEF DESCRIPTION OF THE DRAWINGS

The invention described herein is illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements.

FIG. 9A illustrates a side view of a number of structures that may define, or be located in close proximity to, a stoma channel formed in an ostomy wafer; and FIG. 9B illustrates a magnified view of one of the structures illustrated in FIG. 9A.

DETAILED DESCRIPTION

Figure 1:
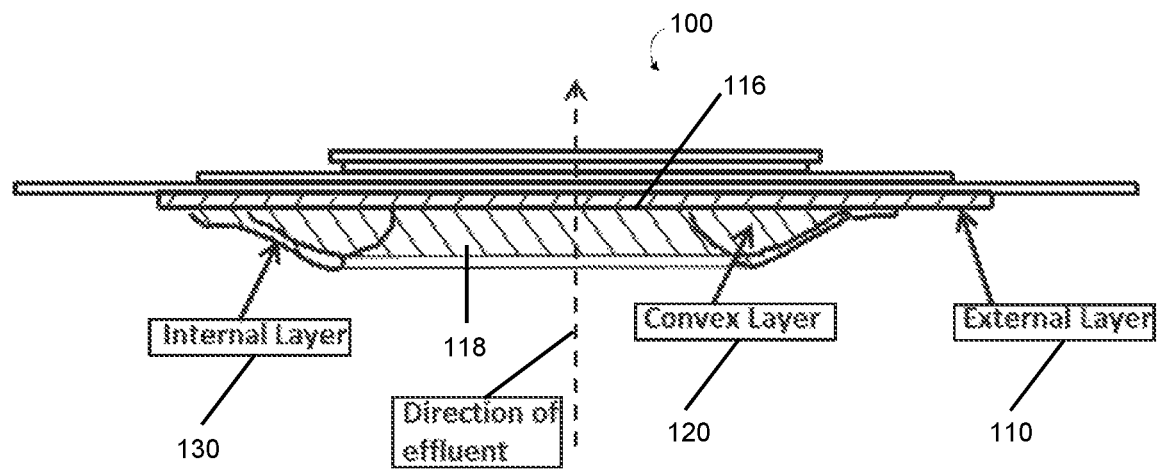
FIG. 1 illustrates a cross-sectional view of one embodiment of an ostomy wafer.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

A number of features described below may be illustrated in the drawings in phantom. Depiction of certain features in phantom is intended to convey that those features may be hidden or present in one or more embodiments, while not necessarily present in other embodiments. Additionally, in the one or more embodiments in which those features may be present, illustration of the features in phantom is intended to convey that the features may have location(s) and/or position(s) different from the locations(s) and/or position(s) shown.

The present disclosure provides ostomy wafers and ostomy devices and/or systems. In some embodiments, the designs, built-in structures, and moldable materials and/or technologies of the ostomy wafers of the present disclosure provide increased comfort, peace of mind, and quality of life to patients. The devices (e.g., ostomy wafers) and methods associated therewith are directed to providing an improved fit to patients (e.g., ostomates) through molding to irregular skin contours and folds, in addition to mating with stomas and peristomal skin surrounding stomas. By molding to irregular skin contours and folds in peristomal regions, at least in some embodiments, the ostomy wafers of the present disclosure provide an efficient and reliable seal/barrier against effluent leakage.

The ostomy wafers of the present disclosure may be adjusted to fit a variety of stomal and/or peristomal skin shapes, contours, conditions, and/or sizes. As such, at least in some embodiments, the production or use of the devices disclosed herein does not require body scanning and personal customization. Instead, the devices disclosed herein are adapted for use with many subjects having different stomal and peristomal topographies.

Certain Terminologies

Unless defined otherwise, all technical and scientific terms used herein are intended to have, or otherwise employ, the same meaning as would be commonly understood by one of ordinary skill in the art to which the subject matter of the present disclosure belongs. It should be appreciated that the foregoing general description and the following examples are exemplary and explanatory only and not restrictive of any subject matter claimed. The use of a singular form herein includes a plural form unless specifically stated otherwise. More specifically, as used in the specification and the appended claims, the singular forms "a," "an" and "the" include plural referents unless the context clearly dictates otherwise. The use of "or" in the present disclosure means "and/or" unless stated otherwise. Furthermore, use of the terms "comprising" and "including" as well as other forms (e.g., "comprise," "comprises," "include," and "includes") is not intended to be limiting.

As used herein, ranges and amounts may be expressed as "about" a particular value or range. The term "about" may also include the exact amount. For example, the expression "about 5 µL" means "about 5 µL" and also "5 µL." Generally, the term "about" includes an amount that would be expected to be within experimental error. More specifically, the term "about" includes values that are within 10% less than to 10% greater than the specified value. In one example, the expression "about 50%" means "between 45% and 55%." In another example, the expression "about 30" means "between 27 and 33."

As used herein, the terms "individual(s)", "subject(s)," and "patient(s)" refer to any mammal. In some embodiments, the mammal may be a human. Of course, it should be appreciated that in other embodiments, the mammal may be a non-human.

For the purposes of the present disclosure, the term "stoma" refers to an opening in the body. Generally, the stoma is a surgical opening in the torso of the body. In some instances, the term "stoma" may also refer to internal tissue, organs, or portions thereof that are exposed by the opening. By way of non-limiting example, internal tissue and/or organs may be selected from the colon, ileum, small intestine, large intestine, jejunum, and duodenum, and combinations thereof. The internal tissue may be an end or a loop of a small or large intestine, for example.

Unless specified otherwise, the term "flush/retracted skin" as used herein refers to any skin surrounding the stoma or opening, whether it be external skin, peristomal skin, or a combination thereof. For the purposes of the present disclosure, the term "external skin" refers to skin that is near the stoma but generally not in contact with internal tissues or effluent. As used herein, the term "peristomal skin" refers to skin that is in contact with internal tissues and/or effluent or skin that is likely to contact effluent.

As used herein, the term "ostomate" refers to a subject that may have use of the ostomy wafers of the present disclosure. While the term "ostomate" typically refers to a subject with a surgical opening, as used herein, the term "ostomate" may refer to a subject who has a stoma, regardless of whether the stoma was created by surgery or other means.

The term "ostomy wafer" may be used interchangeably herein with the terms "adapter," "wafer," or "layered adhesive wafer." Generally, the term "wafer" refers collectively to at least an external layer and a convex layer of the ostomy wafer. Unless otherwise specified, those terms may be used interchangeably. The term "effluent" refers to any internal fluid(s) produced by an ostomate that may be secreted from the stoma or that may exit the stoma.

As used herein, the term "moldable" refers to an elastic, deformable, and/or resilient property, which provides the capability to conform to a stoma and/or form a seal against a stoma. The moldable materials/features of various embodiments disclosed herein may be distinguishable from stretchable and flexible materials, the latter of which may not truly conform to the stoma such that the stretchable and flexible materials may not form a seal against a stoma as contemplated by the present disclosure.

The term "moldable" as used herein may encompass the properties and/or characteristics of malleability and ductility. The shape change of a moldable material in use thereof may be controlled by an external resistive element to cause conformance to a complementary feature. In stoma device/system applications, such moldability may be a highly desirable property to facilitate fitting of devices to the skin and stoma to form better seals and thereby resist leaks.

As used herein, the term "flexible" refers to the elastic deformation of a structure under an external force. Upon removal of the external force, it should be appreciated that the structure will substantially return to its original (previous) geometry. Measurement of flexibility may be quantified in linear displacement (e.g., µm, mm, cm, m, etc.) and expressed with regards to original length/diameter and/or flexed length/diameter. In some embodiments, the second moment of area may influence the deformation experienced by the body, such as the moment associated with the deflection of cantilevered beams, for example.

At least in some embodiments, a device that is moldable may also have the property of flexibility. Flexibility is desirable in ostomy systems to allow contact between a device and the skin/mucosal membranes to be maintained to resist or minimize gaps which may lead to leakage. In use of ostomy devices, flexion of skin/mucosal membranes may occur depending on ostomate activity and/or effluent passage. Rigid devices generally are not able to continually adapt to, and conform to, the skin/mucosal membranes during flexion thereof. However, flexible devices are generally capable of continually adapting to, and conforming to, the skin/mucosal membranes during such flexion.

As used herein, the term "stretchable" refers to the plastic or elastic deformation of a structure due to an applied force that results in an increase in at least one dimension (e.g., length, width, height, etc.) thereof. The cross-sectional area of the structure may influence the deformation experienced by the structure. In one example, the length change of a bar under tensile loading may be influenced by the cross-sectional area and/or shape of the bar. Measurement of such deformation may be in linear displacement (e.g., μm, mm, cm, m, etc.), at least in some embodiments. Stretchable materials may facilitate relatively easy placement over the stoma and maintenance of the stoma seal when the shape of the stoma changes. It should be appreciated that a brittle material generally would not be able to deform without failure (e.g., development of fractures and/or cracks).

The devices and/or systems of the present disclosure may include at least one element that is stretchable, flexible, moldable, and/or a combination thereof. In some embodiments, the devices and/or systems disclosed herein may be characterized as stretchable, flexible, moldable, and/or a combination thereof.

It should be appreciated that the section headings contained herein are employed for organization purposes only. As such, the section headings should not be construed as limiting the subject matter described.

Ostomy Wafers

Ostomy wafers for use in ostomy devices and/or systems are disclosed herein. The ostomy wafers of the present disclosure are designed to adapt or conform to the stoma and surrounding skin, thereby providing an effective barrier against effluent that may leak onto an ostomate's skin, at least in some embodiments. The ostomy wafers disclosed herein minimize leakage to resist skin irritation and breakdown in such a manner that an ostomate may feel more confident in his or her ability to manage his or her stoma. Consequently, when compared to the use and application of other devices, a patient may use and apply the ostomy wafers of the present disclosure with confidence of a lower likelihood of embarrassing leakage, infection, and leakage-related skin damage. Additionally, due at least in part to the moldability, designs, and features thereof, the ostomy wafers of the present disclosure may minimize application time for an array of users. In some embodiments, "all in one" deformation of the ostomy wafers disclosed herein may avoid use of a combination of products, such as pastes and seals, for example, thereby easing (e.g., reducing user training times and user learning curves) the application and removal of the ostomy wafers compared to other configurations. This may be desirable for ostomates because application and removal of ostomy skin barrier products can be a time-consuming process.

Generally, ostomy wafers disclosed herein include an external layer (e.g., the external layers 110, 210, 310, 410 in respective FIGS. 1-4) and a convex layer (e.g., the convex layers 120, 220, 320, 420 in FIGS. 1-4). In some embodiments, the ostomy wafers may include an internal layer (e.g., the internal layer 130 in FIG. 1 or the internal layer 330 in FIG. 3). Of course, it should be appreciated that in some embodiments, the internal layer may be omitted.

In some embodiments, the convex layer of the ostomy wafer may have a greater degree of convexity and/or tapering than in other embodiments. For example, illustrative ostomy wafers 200 and 400 shown in FIGS. 2 and 4, respectively, have corresponding convex layers 220, 420 that have a greater degree of convexity and tapering than convex layers 120, 320 of the corresponding wafers 100, 300. In some situations, the convex layer of the ostomy wafer may contact the base of the ileum or the perimeter of the stoma to lessen the likelihood of effluent seeping underneath the ostomy wafer. In any case, the ostomy wafers depicted in FIGS. 1-4 may be especially advantageous for flush and retracted stomas. It should be appreciated that any of the layers of the ostomy wafers disclosed herein may form or contribute to an effective sealing barrier.

At least a portion of each ostomy wafer of the present disclosure is moldable, malleable, and/or adaptable to provide conformity to the stoma or the surrounding peristomal skin. Conformity to the surrounding peristomal skin generally promotes or provides an effective barrier against effluent leakage. In some embodiments, the ostomy wafers disclosed herein may include one or more compliant layers that are able to conform to unique surface features of an individual. In some examples, the ostomy wafers include a moldable adhesive material, such as Durahesive, Stomahesive, Modified Stomahesive, Duoderm, or a combination thereof, for instance.

Due at least in part to the moldability thereof, the ostomy wafers of the present disclosure generally do not require irreversible physical modification to achieve an appropriate and effective fit for a particular user or patient. In some embodiments, the ostomy wafers may be capable of molding to an individual via multiple mechanisms without the requirement of being cut or torn to accommodate stoma size/shape. The moldable adhesive and/or sealing functions of the ostomy wafer may occur at the skin-wafer interface, the stoma-wafer interface, or a combination thereof.

The ostomy wafers of the present disclosure may be conformable to individuals in several different ways. In one respect, as mentioned above, ostomy wafers disclosed herein, or at least portions thereof, may be moldable or compliant to allow the wafer to deform to unique body contours. In addition to the one or more compliant layers thereof, any of the ostomy wafers disclosed herein may include features, such as ridges, gaps, grooves, profiles, segments, stoma channel built-in structures, and combinations thereof, for example, that further facilitate deformation to unique body contours and provide an effective and comfortable barrier.

A barrier may be established between the stoma and the ostomy wafer that is initiated by the application of pressure to the wafer (i.e., to cause molding of the wafer to the surrounding skin areas) and thereby to the surrounding skin areas, which may cause, or otherwise be associated with, the protrusion of flush or retracted stomas. Thereafter, the barrier may be enhanced through the controlled structural deformation of the ostomy wafer via features such as gaps, ridges and stoma channel built-in structures, for example. Those features may be used as desired at locations where they are most helpful to establish and/or enhance an effective barrier, and to the degree appropriate for the individual and the particular stoma.

In some embodiments, the feature(s) employed to achieve controlled structural deformation of the ostomy wafers may have shapes different from a typical convex form. In some embodiments, those features may allow the ostomy wafers to be tailored to produce different stress distributions within the structure and alter pressure distributions on the user's skin. In embodiments in which greater pressure at the abdomen wall may be desirable for a given application force, that tailoring may be beneficial. Additionally, in some embodiments, that tailoring may permit physically impaired individuals to achieve desirable degrees of ostomy wafer management and ostomy wafer conformity for limited levels of application force.

Gaps and Grooves

Figure 5A:
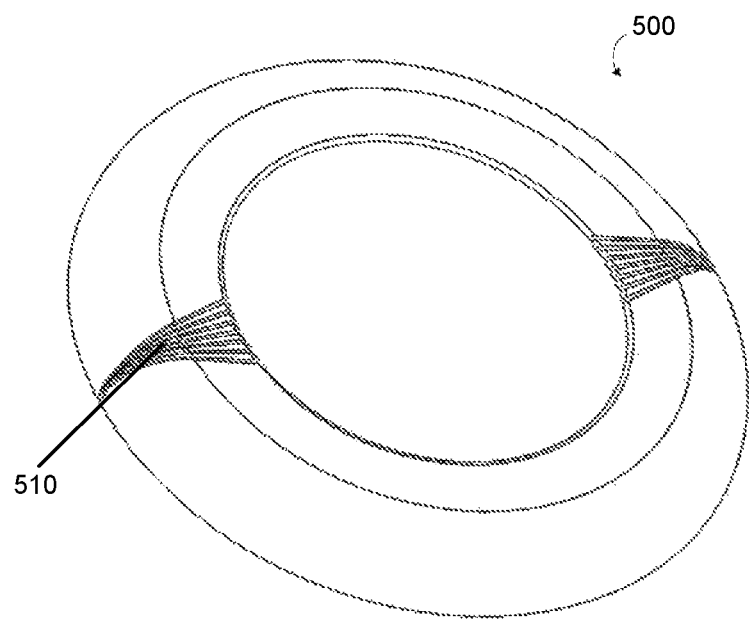
FIG. 5A illustrates a top perspective view of one embodiment of an ostomy wafer with gap(s) or groove(s) that allow the wafer to fold or crease to adapt to a subject's skin topography.
Figure 5B:
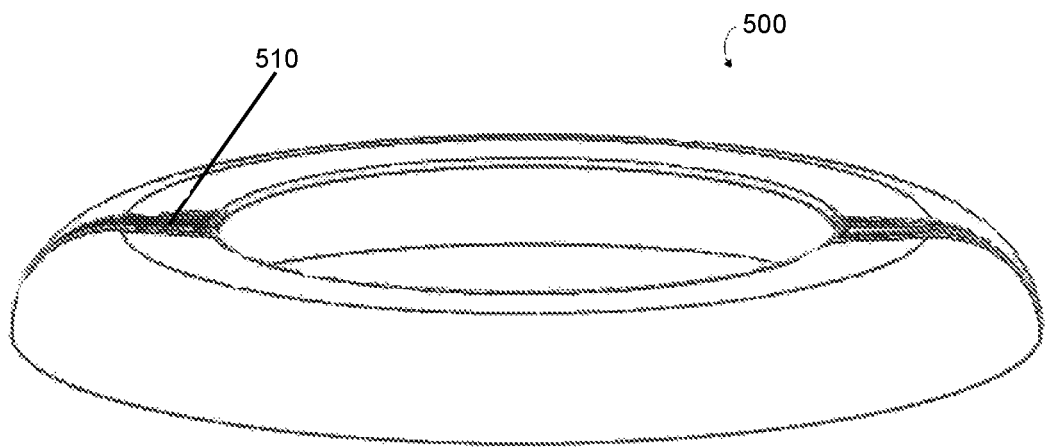
FIG. 5B illustrates a side perspective view of the ostomy wafer illustrated in FIG. 5A.

The ostomy wafer 500 shown in FIGS. 5A and 5B includes one or more grooves 510 formed in at least one layer thereof. As used herein, the term "groove" generally refers to a depression or crease in the wafer/layer having a depth less than the height or thickness of the wafer/layer itself. The ostomy wafer 600 shown in FIGS. 6A and 6B includes one or more gaps 610 formed in the wafer 600 or at least one layer thereof. For the purposes of the present disclosure, the term "gap" generally refers to a break in the wafer/layer having a depth equal to the wafer/layer itself. Of course, it should be appreciated that in some embodiments, the terms "gap" and "groove" may be substantially equivalent and/or interchangeable as references to any break, channel, depression, cutout, notch, or the like formed in any ostomy wafer disclosed herein. The presence of gaps or grooves may define areas of the wafer/layer therebetween that are referred to herein as segments. Gaps or grooves advantageously allow for hinged deformation of the ostomy wafer and facilitate conformity of the ostomy wafer to an ostomate's stoma and surrounding skin.

Figure 6A:
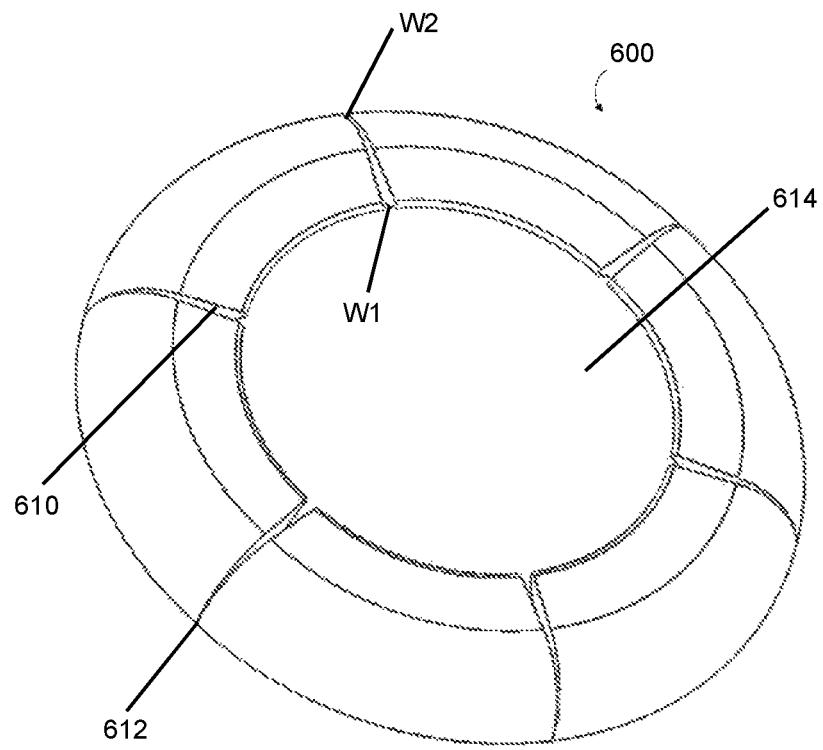
FIG. 6A illustrates a top perspective view of one embodiment of an ostomy wafer with multiple gaps distributed around the wafer to allow deformation in multiple directions.
Figure 6B:
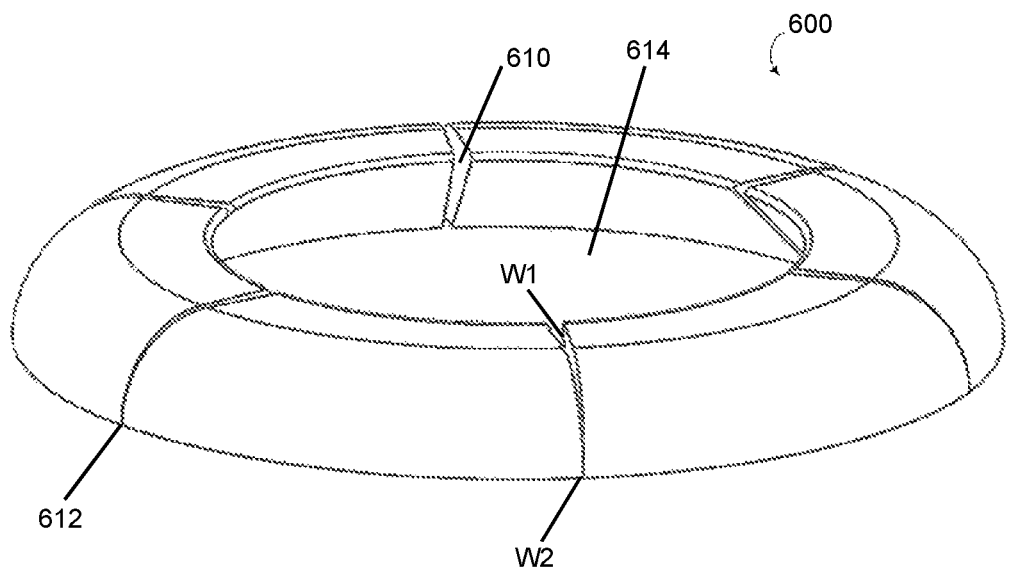
FIG. 6B illustrates a side perspective view of the ostomy wafer illustrated in FIG. 6A.

In some embodiments, one or more gaps formed in the wafer/layer may be relatively small (e.g., see the gaps 610 in FIGS. 6A and 6B). In other embodiments, one or more gaps formed in the wafer/layer may be relatively large (e.g., see the gap 810 of the wafer 800 shown in FIGS. 8A and 8B). Larger gaps may be sized to accommodate a hernia or any suitable protrusion or irregular form. In some embodiments, the gap(s) of the wafer may be small such that at least one segment or portion that defines the gap(s) is more conformable than other segments or portions of the wafer in order to accommodate a hernia, for example.

Gaps and grooves of the ostomy wafers disclosed herein may advantageously provide low stiffness regions that allow for deformation to occur without impingement of other regions of the wafer. In some embodiments, the gaps or grooves may allow for deformation of the wafer such that a portion of the ostomy wafer receives, is filled with, or otherwise accommodates an abdominal area with an atypical shape, such as an area with a large body crease or a hernia, for example.

In some embodiments, the ostomy wafers of the present disclosure include at least one partial gap, meaning that portions of the wafer/layer on either side of the partial gap are connected at least at one point along the gap. In some cases, the portions of the wafer/layer on either side of the partial gap are connected at the outermost edge of the wafer/layer, thereby creating a hinge point or hinge region at the site of connection. Additionally, in some cases, the portions of the wafer/layer on either side of the partial gap are connected only at the outermost edge of the wafer/layer (e.g., see the outermost edge 612 shown in FIGS. 6A and 6B).

In some embodiments, the portions of the wafer/layer that define one or more gaps may be held together by a supporting base plate, collar, flange, or the like. In such embodiments, the portions may not be directly connected to each other (e.g., if the gap(s) are complete break(s) in the wafer/layer) but may instead be directly connected to the base plate, collar, flange, or the like. One or more complete breaks may provide maximum flexibility while securement of the portions to one another via the base plate, collar, flange, or the like may facilitate alignment of the wafer with the stoma. Provision of a base plate, collar, flange, or the like to hold the portions together may also streamline manufacturing. In some embodiments, gaps may be located proximal to the stoma channel (e.g., see the location of gaps 610 relative to the stoma channel 614). Additionally, in some embodiments, gaps may have a first width (e.g., see width W1 in FIGS. 6A and 6B) proximal to the stoma channel and second width (e.g., see width W2 in FIGS. 6A and 6B) proximal to the outermost, distal edge of the wafer that is less than the first width.

In some embodiments, each gap may be characterized by a width or an arc in a dimension perpendicular to a radial direction of the gap (e.g., an axial dimension of the wafer). In such embodiments, the arcs of the gaps may range from about 0.1 mm to about 100 mm. In one respect, the arcs of the gaps may range from about 0.1 mm to about 10 mm. In another respect, the arcs of the gaps may range from about 10 mm to about 100 mm. Additionally, in such embodiments, the arcs of the gaps may be greater at the outer edge of the ostomy wafer than the arcs of the gaps nearest the stoma channel. In one example, the arcs of the gaps at the outer edge may be as great as 100 mm, and the arcs of the gaps closest to the stoma channel may be as small as 0.1 mm. In other embodiments, however, the arcs of the gaps may be smaller at the outer edge of the ostomy wafer than the arcs of the gaps nearest the stoma channel. In one example, the arcs of the gaps at the outer edge of the ostomy wafer may be as small as 0.1 mm, and the arcs of the gaps closest to the stoma channel may be as great as 10 mm.

In some embodiments, the ostomy wafers disclosed herein include a plurality of gaps or grooves. In one example, ostomy wafers of the present disclosure include at least one gap and at least one groove. In another example, ostomy wafers disclosed herein include a combination of a plurality of gaps and a plurality of grooves.

Generally, gaps and grooves impart a greater degree of flexibility to the ostomy wafers of the present disclosure than configurations of ostomy wafers incorporating other features. Numerous gaps or grooves (e.g., more than about five gaps or grooves) may be ideal for an ostomate who is active and requires functionality of the ostomy device across a wide range of motion and activity. In contrast, fewer gaps or grooves (e.g., about five or less gaps or grooves) may be more suitable for an ostomate who requires more support in the ostomy device and is less active. For example, an ostomate having folds of fat/skin surrounding the stoma may require more support in the device while still requiring some flexibility imparted by a few gaps or grooves.

In some embodiments, ostomy wafers disclosed herein include at least one gap or groove. In one example, ostomy wafers of the present disclosure include at least two gaps or grooves. In another example, ostomy wafers of the present disclosure include at least three gaps or grooves. In yet another example, ostomy wafers of the present disclosure include at least four gaps or grooves. In yet another example still, ostomy wafers of the present disclosure include at least five gaps or grooves. Further, ostomy wafers of the present disclosure include at least six gaps or grooves, at least in some embodiments. Further still, ostomy wafers of the present disclosure include at least eight gaps or grooves, at least in some embodiments. Finally, in some embodiments, ostomy wafers of the present disclosure include at least ten gaps or grooves.

In some embodiments, ostomy wafers disclosed herein include between one gap or groove and one hundred gaps or grooves. In one example, ostomy wafers disclosed herein include between one gap or groove and fifty gaps or grooves. In another example, ostomy wafers disclosed herein include between one gap or groove and twenty gaps or grooves. In yet another example, ostomy wafers disclosed herein include between one gap or groove and ten gaps or grooves. In yet another example still, ostomy wafers disclosed herein include between two gaps or grooves and one hundred gaps or grooves. Further, ostomy wafers disclosed herein include between two gaps or grooves and fifty gaps or grooves, at least in some embodiments. Further still, ostomy wafers disclosed herein include between two gaps or grooves and twenty gaps or grooves, at least in some embodiments. Additionally, ostomy wafers disclosed herein include between two gaps or grooves and ten gaps or grooves, at least in some embodiments. In some embodiments, ostomy wafers disclosed herein include between five gaps or grooves and one hundred gaps or grooves. Furthermore, in some embodiments, ostomy wafers disclosed herein include between five gaps or grooves and fifty gaps or grooves. Further still, in some embodiments, ostomy wafers disclosed herein include between five gaps or grooves and twenty gaps or grooves. Finally, in some embodiments, ostomy wafers disclosed herein include between five gaps or grooves and ten gaps or grooves.

In some embodiments, ostomy wafers disclosed herein include a plurality of gaps and/or grooves that are evenly distributed over the radial area of the ostomy wafer or a layer thereof. Additionally, in some embodiments, ostomy wafers of the present disclosure include a plurality of gaps and/or grooves that are focused in one or more locations and unevenly distributed over the radial area of the ostomy wafer or a layer thereof. For the purposes of the present disclosure, the term "radial area" refers to the area of the body-contacting surface of the ostomy wafer or a layer thereof.

In some embodiments, ostomy wafers disclosed herein include a plurality of gaps and/or grooves that are distributed over less than 5% of the radial area of the ostomy wafer or a layer thereof. Additionally, in some embodiments, ostomy wafers disclosed herein include a plurality of gaps and/or grooves that are distributed over less than 10% of the radial area of the ostomy wafer or a layer thereof. Further, in some embodiments, ostomy wafers disclosed herein include a plurality of gaps and/or grooves that are distributed over less than 15% of the radial area of the ostomy wafer or a layer thereof. Further, in some embodiments still, ostomy wafers disclosed herein include a plurality of gaps and/or grooves that are distributed over less than 20% of the radial area of the ostomy wafer or a layer thereof. Finally, in some embodiments yet still, ostomy wafers disclosed herein include a plurality of gaps and/or grooves that are distributed over less than 25% of the radial area of the ostomy wafer or a layer thereof.

In some embodiments, ostomy wafers of the present disclosure include a plurality of gaps and/or grooves that are distributed over less than 30% of the radial area of the ostomy wafer or a layer thereof. Additionally, in some embodiments, ostomy wafers of the present disclosure include a plurality of gaps and/or grooves that are distributed over less than 35% of the radial area of the ostomy wafer or a layer thereof. Further, in some embodiments, ostomy wafers of the present disclosure include a plurality of gaps and/or grooves that are distributed over less than 40% of the radial area of the ostomy wafer or a layer thereof. Further, in some embodiments still, ostomy wafers of the present disclosure include a plurality of gaps and/or grooves that are distributed over less than 45% of the radial area of the ostomy wafer or a layer thereof. In some embodiments yet still, ostomy wafers of the present disclosure include a plurality of gaps and/or grooves that are distributed over less than 50% of the radial area of the ostomy wafer or a layer thereof. Finally, in some embodiments, ostomy wafers of the present disclosure include a plurality of gaps and/or grooves that are distributed over less than 55% of the radial area of the ostomy wafer or a layer thereof.

In some embodiments, the plurality of gaps and/or grooves of the ostomy wafers disclosed herein are distributed over more than 10% of the radial area of the ostomy wafer or a layer thereof. Additionally, in some embodiments, the plurality of gaps and/or grooves of the ostomy wafers disclosed herein are distributed over more than 20% of the radial area of the ostomy wafer or a layer thereof. Further, in some embodiments, the plurality of gaps and/or grooves of the ostomy wafers disclosed herein are distributed over more than 30% of the radial area of the ostomy wafer or a layer thereof. Further, in some embodiments still, the plurality of gaps and/or grooves are distributed over more than 40% of the radial area of the ostomy wafer or a layer thereof. In some embodiments yet still, the plurality of gaps and/or grooves of the ostomy wafers disclosed herein are distributed over more than 50% of the radial area of the ostomy wafer or a layer thereof. Furthermore, in some embodiments, the plurality of gaps and/or grooves of the ostomy wafers disclosed herein are distributed over more than 60% of the radial area of the ostomy wafer or a layer thereof. Finally, in some embodiments, the plurality of gaps and/or grooves of the ostomy wafers disclosed herein are distributed over more than 70% of the radial area of the ostomy wafer or a layer thereof.

In some embodiments, one or more ostomy wafers disclosed herein, or the convex layer(s) of the one or more ostomy wafers, include a first gap or groove and a second gap or groove. In one example, the first gap/groove and the second gap/groove may be separated by at least 1% of the radial area of the ostomy wafer or a layer thereof. In another example, the first gap/groove and the second gap/groove may be separated by at least 2% of the radial area of the ostomy wafer or a layer thereof. In yet another example, the first gap/groove and the second gap/groove may be separated by at least 3% of the radial area of the ostomy wafer or a layer thereof. In yet another example still, the first gap/groove and the second gap/groove may be separated by at least 4% of the radial area of the ostomy wafer or a layer thereof. Further, in some embodiments, the first gap/groove and the second gap/groove may be separated by at least 5% of the radial area of the ostomy wafer or a layer thereof. Further, in some embodiments still, the first gap/groove and the second gap/groove may be separated by at least 10% of the radial area of the ostomy wafer or a layer thereof. Finally, in some embodiments, the first gap/groove and the second gap/groove may be separated by at least 15% of the radial area of the ostomy wafer or a layer thereof.

In some embodiments, the first gap/groove and the second gap/groove of one or more ostomy wafers of the present disclosure may be separated by at least 20% of the radial area of the ostomy wafer or a layer thereof. Additionally, in some embodiments, the first gap/groove and the second gap/groove may be separated by at least 25% of the radial area of the ostomy wafer or a layer thereof. In some embodiments still, the first gap/groove and the second gap/groove may be separated by at least 30% of the radial area of the ostomy wafer or a layer thereof. In some embodiments yet still, the first gap/groove and the second gap/groove may be separated by at least 35% of the radial area of the ostomy wafer or a layer thereof. Further, in some embodiments, the first gap/groove and the second gap/groove may be separated by at least 40% of the radial area of the ostomy wafer or a layer thereof. Further, in some embodiments still, the first gap/groove and the second gap/groove may be separated by at least 45% of the radial area of the ostomy wafer or a layer thereof. Finally, in some embodiments, the first gap/groove and the second gap/groove may be separated by at least 50% of the radial area of the ostomy wafer or a layer thereof.

In some embodiments, a gap or groove formed in one or more of the ostomy wafers of the present disclosure has a width from about 0.01 mm to about 1 cm. Additionally, in some embodiments, the gap or groove has a width from about 0.1 mm to about 500 mm. In some embodiments still, the gap or groove has a width from about 0.2 mm to about 250 mm. In some embodiments yet still, the gap or groove has a width from about 0.5 mm to about 100 mm. Further, in some embodiments, the gap or groove has a width from about 1 mm to about 50 mm. Further, in some embodiments still, the gap or groove has a single width along its length. In other embodiments, however, the gap or groove width varies along its length.

Ridges

Figure 7A:
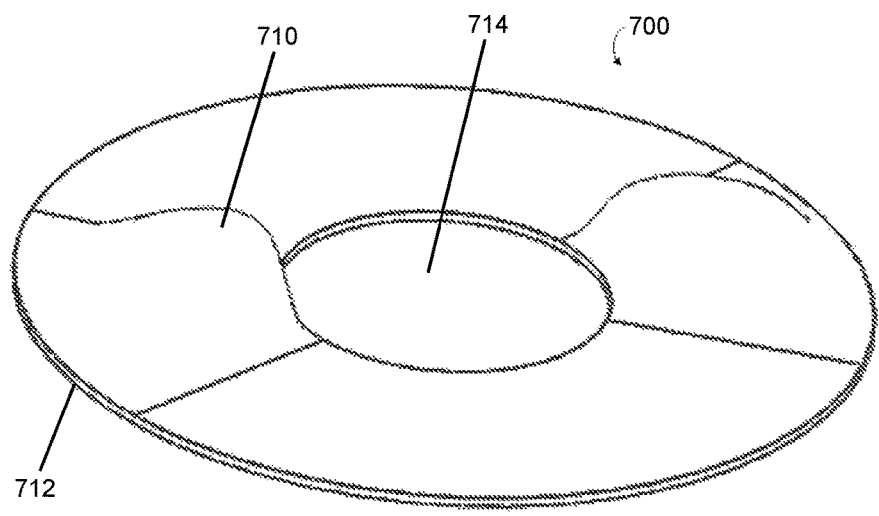
FIG. 7A illustrates a top perspective view of one embodiment of an ostomy wafer with twin raised sections capable of being received in creases of a subject's skin.
Figure 7B:
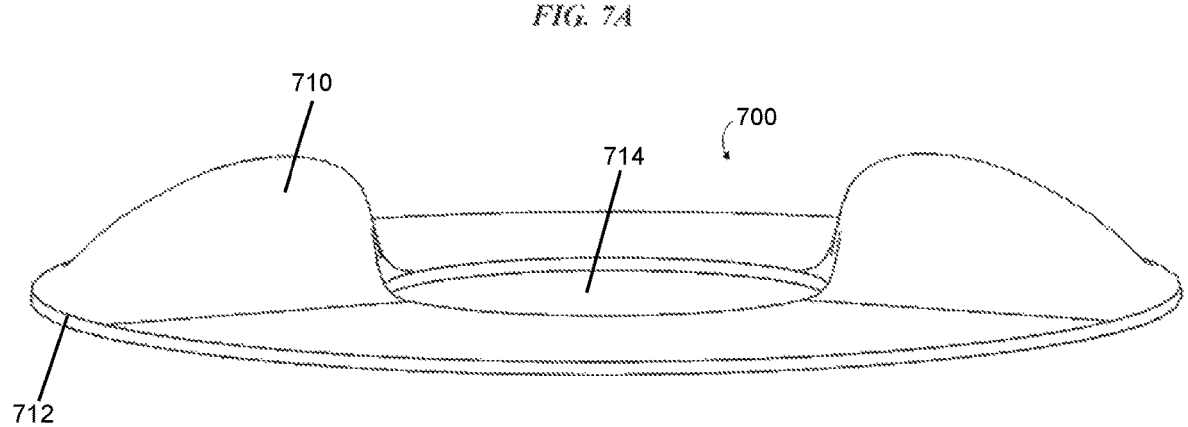
FIG. 7B illustrates a side perspective view of the ostomy wafer illustrated in FIG. 7A.

As shown in FIGS. 7A and 7B, one or more ostomy wafers 700 include at least one ridge 710 formed in one or more layers thereof. As contemplated herein, ridges such as the ridge 710 generally protrude from the ostomy wafer (e.g., the ostomy wafer 700) toward the body-facing side of the ostomy wafer so as to be received in and/or fill creases or folds in a patient's skin topography. It should be appreciated that ridges disclosed herein may extend in virtually any desired direction along the ostomy wafer surface or a layer thereof. In some embodiments, the ridge 710 extends radially from the stoma channel (e.g., the stoma channel 714) all the way to the outer edge (e.g., the outer edge 712) of the convex layer. Additionally, in some embodiments, the ridge extends partway from the stoma channel toward the outer edge of the convex layer. In one example, the ridge is curved. In another example, the ridge is straight or planar. In some embodiments, the ridge is rigid. In other embodiments, however, the ridge is flexible. In such embodiments, the ridge may have a flexibility similar to cartilage.

In some embodiments, the at least one ridge of the one of more ostomy wafers of the present disclosure has a single height along its length. In other embodiments, however, the ridge height varies along its length. In one example, the ridge has a height from about 0.2 cm to about 5 cm. In another example, the ridge has a height from about 0.2 cm to about 4.5 cm. In yet another example, the ridge has a height from about 0.2 cm to about 4 cm. In yet another example still, the ridge has a height from about 0.2 cm to about 3.5 cm. Finally, in another example, the ridge has a height from about 0.2 cm to about 3 cm.

In another example, the at least one ridge of the one of more ostomy wafers of the present disclosure has a height from about 0.5 cm to about 4.5 cm. In yet another example, the ridge has a height from about 0.5 cm to about 4 cm. In yet another example still, the ridge has a height from about 0.5 cm to about 3.5 cm. Finally, in another example, the ridge has a height from about 0.5 cm to about 3 cm.

In some embodiments, ostomy wafers disclosed herein include at least one ridge. Additionally, in some embodiments, ostomy wafers disclosed herein include at least two ridges. In some embodiments still, ostomy wafers disclosed herein include at least three ridges. In some embodiments yet still, ostomy wafers disclosed herein include at least four ridges. Further, in some embodiments, ostomy wafers disclosed herein include at least five ridges. Further, in some embodiments still, ostomy wafers disclosed herein include at least six ridges. Further, in some embodiments yet still, ostomy wafers disclosed herein include at least eight ridges. Finally, in some embodiments, ostomy wafers disclosed herein include at least ten ridges.

In some embodiments, ostomy wafers disclosed herein include between one ridge and one hundred ridges. Additionally, in some embodiments, ostomy wafers disclosed herein include between one ridge and fifty ridges. In some embodiments still, ostomy wafers disclosed herein include between one ridge and twenty ridges. In some embodiments yet still, ostomy wafers disclosed herein include between one ridge and ten ridges.

In some embodiments, ostomy wafers disclosed herein include between two ridges and one hundred ridges. Additionally, in some embodiments, ostomy wafers disclosed herein include between two ridges and fifty ridges. In some embodiments still, ostomy wafers disclosed herein include between two ridges and twenty ridges. In some embodiments yet still, ostomy wafers disclosed herein include between two ridges and ten ridges.

In some embodiments, ostomy wafers disclosed herein include between five ridges and one hundred ridges. Additionally, in some embodiments, ostomy wafers disclosed herein include between five ridges and fifty ridges. In some embodiments still, ostomy wafers disclosed herein include between five ridges and twenty ridges. In some embodiments yet still, ostomy wafers disclosed herein include between five ridges and ten ridges.

In some embodiments, ostomy wafers disclosed herein include a plurality of ridges that are evenly distributed over the radial area of the ostomy wafer or a layer thereof. In other embodiments, ostomy wafers disclosed herein include a plurality of ridges that are focused in a first location and unevenly distributed over the radial area of the ostomy wafer or a layer thereof. For the purposes of the present disclosure, the term "radial area" refers to the area of the body-contacting surface of the ostomy wafer or a layer thereof.

In some embodiments, ostomy wafers of the present disclosure include a plurality of ridges that are distributed over less than 5% of the radial area of the ostomy wafer or a layer thereof. Additionally, in some embodiments, ostomy wafers of the present disclosure include a plurality of ridges that are distributed over less than 10% of the radial area of the ostomy wafer or a layer thereof. In some embodiments still, ostomy wafers of the present disclosure include a plurality of ridges that are distributed over less than 15% of the radial area of the ostomy wafer or a layer thereof. In some embodiments yet still, ostomy wafers of the present disclosure include a plurality of ridges that are distributed over less than 20% of the radial area of the ostomy wafer or a layer thereof. Finally, in some embodiments, ostomy wafers of the present disclosure include a plurality of ridges that are distributed over less than 26% of the radial area of the ostomy wafer or a layer thereof.

In some embodiments, ostomy wafers disclosed herein include a plurality of ridges that are distributed over less than 30% of the radial area of the ostomy wafer or a layer thereof. Additionally, in some embodiments, ostomy wafers disclosed herein include a plurality of ridges that are distributed over less than 35% of the radial area of the ostomy wafer or a layer thereof. In some embodiments still, ostomy wafers disclosed herein include a plurality of ridges that are distributed over less than 40% of the radial area of the ostomy wafer or a layer thereof. In some embodiments yet still, ostomy wafers disclosed herein include a plurality of ridges that are distributed over less than 45% of the radial area of the ostomy wafer or a layer thereof. Further, in some embodiments, ostomy wafers disclosed herein include a plurality of ridges that are distributed over less than 50% of the radial area of the ostomy wafer or a layer thereof. Finally, in some embodiments, ostomy wafers disclosed herein include a plurality of ridges that are distributed over less than 55% of the radial area of the ostomy wafer or a layer thereof.

In some embodiments, the plurality of ridges of the ostomy wafers disclosed herein are distributed over more than 10% of the radial area of the ostomy wafer or a layer thereof. Additionally, in some embodiments, the plurality of ridges are distributed over more than 20% of the radial area of the ostomy wafer or a layer thereof. In some embodiments still, the plurality of ridges are distributed over more than 30% of the radial area of the ostomy wafer or a layer thereof. In some embodiments yet still, the plurality of ridges are distributed over more than 40% of the radial area of the ostomy wafer or a layer thereof. Further, in some embodiments, the plurality of ridges are distributed over more than 50% of the radial area of the ostomy wafer or a layer thereof. Further, in some embodiments yet still, the plurality of ridges are distributed over more than 60% of the radial area of the ostomy wafer or a layer thereof. Finally, in some embodiments, the plurality of ridges are distributed over more than 70% of the radial area of the ostomy wafer or a layer thereof.

In some embodiments, one or more ostomy wafers disclosed herein, or the convex layer(s) of the one or more ostomy wafers, include a first ridge and a second ridge. In one example, the first ridge and the second ridge may be separated by at least 1% of the radial area of the ostomy wafer or a layer thereof. In another example, the first ridge and the second ridge may be separated by at least 2% of the radial area of the ostomy wafer or a layer thereof. In yet another example, the first ridge and the second ridge may be separated by at least 3% of the radial area of the ostomy wafer or a layer thereof. In yet another example still, the first ridge and the second ridge may be separated by at least 4% of the radial area of the ostomy wafer or a layer thereof. Additionally, in some embodiments, the first ridge and the second ridge may be separated by at least 5% of the radial area of the ostomy wafer or a layer thereof. In some embodiments still, the first ridge and the second ridge may be separated by at least 10% of the radial area of the ostomy wafer or a layer thereof. In some embodiments yet still, the first ridge and the second ridge may be separated by at least 15% of the radial area of the ostomy wafer or a layer thereof.

In some embodiments, the first ridge and the second ridge of the one or more ostomy wafers disclosed herein may be separated by at least 20% of the radial area of the ostomy wafer or a layer thereof. Additionally, in some embodiments, the first ridge and the second ridge may be separated by at least 25% of the radial area of the ostomy wafer or a layer thereof. In some embodiments still, the first ridge and the second ridge may be separated by at least 30% of the radial area of the ostomy wafer or a layer thereof. In some embodiments yet still, the first ridge and the second ridge may be separated by at least 35% of the radial area of the ostomy wafer or a layer thereof. Further, in some embodiments, the first ridge and the second ridge may be separated by at least 40% of the radial area of the ostomy wafer or a layer thereof. Further, in some embodiments still, the first ridge and the second ridge may be separated by at least 45% of the radial area of the ostomy wafer or a layer thereof. Finally, in some embodiments, the first ridge and the second ridge may be separated by at least 50% of the radial area of the ostomy wafer or a layer thereof.

Profiles

Figures 8A, 8B:
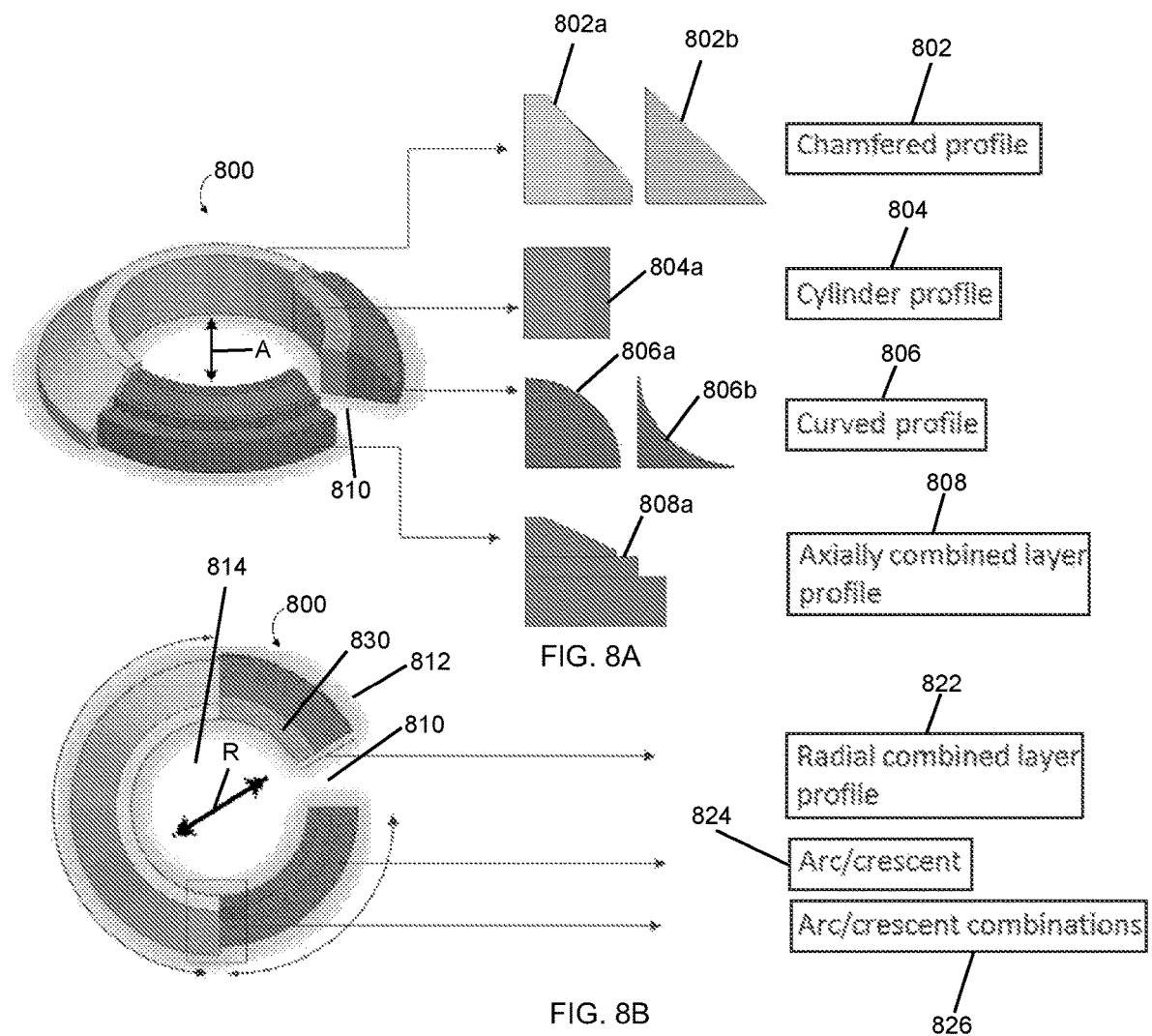
FIG. 8A illustrates a top perspective view of one embodiment of a tapered ostomy wafer having a variety of structures, shapes, and/or profiles.
FIG. 8B illustrates a top view of the ostomy wafer illustrated in FIG. 8A.

In the illustrative embodiment, one or more layers of the ostomy wafers of the present disclosure may have a variety of profiles and/or geometric forms. As shown in FIGS. 8A, an ostomy wafer 800 may include at least one layer having one of the following profiles, or a combination thereof: (i) a chamfered profile 802 (e.g., the chamfered profile 802a or 802b); (ii) a cylindrical or annular profile 804 (e.g., having a rectangular cross-section 804a); (iii) a curved profile 806 (e.g., the convex profile 806a or the concave profile 806b); and (iv) a profile 808 in which multiple features or profiles are combined in an axial direction indicated by arrow A (e.g., the stepped or axially combined layer profile 808a). Additionally, as shown in FIG. 8B, an ostomy wafer 800 may include at least one layer having one of the following profiles, or a combination thereof: (a) a profile 822 in which multiple features or profiles are combined in a radial direction indicated by arrow R; (b) a profile 824 characterized by a single arc and/or crescent; and (c) a profile 826 characterized by a combination of arcs and/or crescents.

Chamfered profiles (e.g., the chamfered profiles 802a, 802b) may provide a continuous profile to promote a gradual pressure increase over the ostomy wafer between the stoma and the outer edge of the wafer during application of the wafer to the patient. Due to that gradual pressure increase, substantially no abrupt transitions or pressure increases occur between high and low pressure areas, and consequently, users may be less likely to experience impingement during activities when ostomy wafers having chamfered profiles are applied to the users. Such wafers may therefore be associated with lower peak stresses, a greater range of mobility, and a more comfortable range of user motion than ostomy wafers having other profiles.

Cylindrical profiles (e.g., the cylindrical profile 804) may provide a stepped or plateaued pressure profile with regions of high pressure and low pressure on the user's skin. If a user has a complex stomal environment (e.g., hernias, damaged skin, post-operative scars, etc.) and needs to limit or avoid pressure on a certain area, the stepped or plateaued pressure profile associated with the cylindrical profile may facilitate accurate and/or precise application of high pressure to specific areas of the stomal environment with limited application of high pressure to other areas.

Curved profiles (e.g., the convex profile 806a and the concave profile 806b) may provide a continuous profile to promote a gradual pressure increase over the ostomy wafer between the stoma and the outer edge of the wafer during application of the wafer to the patient. As a result, curved profiles may reliably provide comfort to the patient wearing the ostomy wafer. Additionally, because substantially no abrupt transitions or pressure increases occur between high and low pressure areas when ostomy wafers having curved profiles are applied to users, users may be less likely to experience impingement during activities. Furthermore, curved profiles may provide altered or adjusted pressure distributions to accommodate gross topographical features, such as skin folds, for example. Finally, since curved profiles may facilitate greater pressure application to the stoma and/or locations adjacent thereto, curved profiles may be particularly suited to retracted stomas and/or complex peristomal environments.

Profiles in which one or more features or profiles are combined in the axial direction A (e.g., the axially combined layer profile 808a) may alter the locations where stepped pressure transitions occur on the subject. The use of wafers having axially combined profiles may avoid application of textured materials and/or edges of ostomy wafers to areas with complex environments (e.g., hernias, damaged skin, scars, etc.). The use of wafers having axially combined profiles may avoid application of excessive pressure to areas containing hernias, damaged skin, or scars. The use of wafers having axially combined profiles may allow smooth pressure transition to accommodate complex environments.

Profiles in which one or more features or profiles are combined in the radial direction R (e.g., the radially combined layer profile 822) may include one or more compliant regions to facilitate recovery of short term damage to a patient's skin or to a stoma. In some embodiments, the compliant region may be a region proximal to the stoma channel (e.g., the region 830 proximal to the stoma channel 814). In other embodiments, however, the compliant region may be a region proximal to the outermost edge of the ostomy wafer (e.g., the outer edge 812). The compliant region may be more flexible, stretchable, moldable, softer, and/or thinner than a less compliant region of the ostomy wafer, at least in some embodiments. In some embodiments, a segment or region of a radially combined layer profile of an ostomy wafer may be less compliant than a more compliant region of the ostomy wafer, thereby providing greater pressure to the skin and/or stoma to cause an inverted stoma to protrude.

Profiles in which one or more features or profiles are combined in the radial direction R (e.g., the radially combined layer profile 822) may result in, or otherwise be associated with, multiple segments of the wafer having different profiles such that the device may referred to as a segmented device. Segmented devices may allow for variable deformations (e.g., different parts of the device can deform and adapt to different areas of the patients) in use thereof. In some embodiments, radially combined layer profiles may be associated with at least two segments that have different profiles. Additionally, in some embodiments, radially combined layer profiles may be associated with at least three segments that have different profiles. In some embodiments still, radially combined layer profiles may be associated with at least four segments that have different profiles. In some embodiments yet still, radially combined layer profiles may be associated with at least ten segments that have different profiles.

Profiles in which one or more features or profiles are combined in the radial direction R (e.g., the radially combined layer profile 822) may allow the ostomy wafer to provide support (or malleability) depending on the particular user. In some embodiments, the segmented devices may be customized to the skin topography of the stoma and the surrounding skin of a particular user. Such customization may provide improved comfort and/or facilitate establishment of a seal between the patient and the device to resist leakage. In some embodiments, segmented devices may also allow for "all in one" deformation, as opposed to the use of a combination of products, such as adhesive solutions (e.g., pastes, glues, seals), for example. Additionally, in some embodiments, segmented devices may substantially negate the use of adhesive solutions or substantially diminish the need for adhesive solutions. As a result, the segmented devices may be easier to apply (and remove) than those used with adhesive solutions. Significantly, avoidance of adhesive solutions may reduce user training times and learning curves.

In some embodiments, the ostomy wafers disclosed herein include a combination of profiles. At least a portion of one or more ostomy wafers of the present disclosure includes an axially combined layer profile (e.g., the axially combined layer profile 808). In addition to the axially combined layer profile, at least a portion of one or more ostomy wafers of the present disclosure includes a radially combined layer profile (e.g., the radially combined layer profile 822).

In some embodiments, ostomy wafers disclosed herein have continuous profiles. In one example, layers of the ostomy wafers disclosed herein have discrete profiles. Continuous profiles may be described in the form of polynomials which include, but are not limited to, $y=mx+C$ and $y=mx^n+C$, where m and n are positive or negative values ranging from $-10$ to $+10$. In some embodiments, discrete profiles may have a ratio no greater than 5:1 (proximal end:distal end) at each step. As such, ostomy wafers having discrete profiles may easily conform to an individual's unique contours.

Segments

The ostomy wafers of the present disclosure include a plurality of segments (e.g., at least two segments) that possess different properties, materials, designs, or structures. The plurality of segments allow for various deformations of the ostomy wafers. As a result, the plurality of segments allow the ostomy wafers to provide support and/or malleability depending on the requirements of the user. In some embodiments, the segments are relatively seamless without any distinguishable structure or feature separating the segments. In other embodiments, however, the segments are separated from another by features such as the gaps, grooves, and ridges described herein, for example. Additionally, in some embodiments, the segments include features such as the gaps, grooves, and ridges described herein, for instance.

In some embodiments, the plurality of segments include at least two axial segments that are stacked in the axial direction A. In some embodiments, axial segments may be likened to stacked rings. Additionally, in some embodiments, the plurality of segments include at least two radial segments that are concentric with one another. In some embodiments, radial segments may be likened to rings in a pond. In some embodiments still, the plurality of segments include at least two parallel segments that radiate outward from the center of the ostomy wafer. In some embodiments, the parallel segments may be likened to petals of a flower.

In some embodiments, ostomy wafers disclosed herein include at least two segments. Additionally, in some embodiments, ostomy wafers disclosed herein include at least three segments. In some embodiments still, ostomy wafers disclosed herein include at least four segments. In some embodiments yet still, ostomy wafers disclosed herein include at least five segments. Further, in some embodiments, ostomy wafers disclosed herein include at least six segments. Further, in some embodiments still, ostomy wafers disclosed herein include at least eight segments. Finally, in some embodiments, ostomy wafers disclosed herein include at least ten segments.

In some embodiments, ostomy wafers disclosed herein include between two segments and one hundred segments. Additionally, in some embodiments, ostomy wafers disclosed herein include between two segments and fifty segments. In some embodiments still, ostomy wafers disclosed herein include between two segments and twenty segments. In some embodiments yet still, ostomy wafers disclosed herein include between two segments and ten segments.

In some embodiments, ostomy wafers disclosed herein include between three segments and one hundred segments. Additionally, in some embodiments, ostomy wafers disclosed herein include between three segments and fifty segments. In some embodiments still, ostomy wafers disclosed herein include between three segments and twenty segments. In some embodiments yet still, ostomy wafers disclosed herein include between three segments and ten segments.

In some embodiments, ostomy wafers disclosed herein include between five segments and one hundred segments. Additionally, in some embodiments, ostomy wafers disclosed herein include between five segments and fifty segments. In some embodiments still, ostomy wafers disclosed herein include between five segments and twenty segments. In some embodiments yet still, ostomy wafers disclosed herein include between five segments and ten segments.

In some embodiments, ostomy wafers disclosed herein include a plurality of segments that are evenly distributed over the radial area of the ostomy wafer or a layer thereof. In other embodiments, ostomy wafers disclosed herein include a plurality of segments that are focused in a first location and unevenly distributed over the radial area of the ostomy wafer or a layer thereof. For the purposes of the present disclosure, the term "radial area" refers to the area of the body-contacting surface of the ostomy wafer or a layer thereof.

In some embodiments, ostomy wafers disclosed herein include a plurality of segments that are distributed over less than 5% of the radial area of the ostomy wafer or a layer thereof. Additionally, in some embodiments, ostomy wafers disclosed herein include a plurality of segments that are distributed over less than 10% of the radial area of the ostomy wafer or a layer thereof. In some embodiments still, ostomy wafers disclosed herein include a plurality of segments that are distributed over less than 15% of the radial area of the ostomy wafer or a layer thereof. In some embodiments yet still, ostomy wafers disclosed herein include a plurality of segments that are distributed over less than 20% of the radial area of the ostomy wafer or a layer thereof. Finally, in some embodiments, ostomy wafers disclosed herein include a plurality of segments that are distributed over less than 26% of the radial area of the ostomy wafer or a layer thereof.

In some embodiments, ostomy wafers disclosed herein include a plurality of segments that are distributed over less than 30% of the radial area of the ostomy wafer or a layer thereof. Additionally, in some embodiments, ostomy wafers disclosed herein include a plurality of segments that are distributed over less than 35% of the radial area of the ostomy wafer or a layer thereof. In some embodiments still, ostomy wafers disclosed herein include a plurality of segments that are distributed over less than 40% of the radial area of the ostomy wafer or a layer thereof. In some embodiments yet still, ostomy wafers disclosed herein include a plurality of segments that are distributed over less than 45% of the radial area of the ostomy wafer or a layer thereof. Further, in some embodiments, ostomy wafers disclosed herein include a plurality of segments that are distributed over less than 50% of the radial area of the ostomy wafer or a layer thereof. Finally, in some embodiments, ostomy wafers disclosed herein include a plurality of segments that are distributed over less than 55% of the radial area of the ostomy wafer or a layer thereof.

In some embodiments, the plurality of segments of the ostomy wafers disclosed herein are distributed over more than 10% of the radial area of the ostomy wafer or a layer thereof. Additionally, in some embodiments, the plurality of segments are distributed over more than 20% of the radial area of the ostomy wafer or a layer thereof. In some embodiments still, the plurality of segments are distributed over more than 30% of the radial area of the ostomy wafer or a layer thereof. In some embodiments yet still, the plurality of segments are distributed over more than 40% of the radial area of the ostomy wafer or a layer thereof. Further, in some embodiments, the plurality of segments are distributed over more than 50% of the radial area of the ostomy wafer or a layer thereof. Further, in some embodiments still, the plurality of segments are distributed over more than 60% of the radial area of the ostomy wafer or a layer thereof. Finally, in some embodiments, the plurality of segments are distributed over more than 70% of the radial area of the ostomy wafer or a layer thereof.

In some embodiments, the ostomy wafers of the present disclosure (or the convex layers thereof) include a first segment and a second segment. In one example, the first segment and the second segment may be separated by at least 1% of the radial area of the ostomy wafer or a layer thereof. In another example, the first segment and the second segment may be separated by at least 2% of the radial area of the ostomy wafer or a layer thereof. In yet another example, the first segment and the second segment may be separated by at least 3% of the radial area of the ostomy wafer or a layer thereof. In yet another example still, the first segment and the second segment may be separated by at least 4% of the radial area of the ostomy wafer or a layer thereof. Further, in another example, the first segment and the second segment may be separated by at least 5% of the radial area of the ostomy wafer or a layer thereof. Further, in yet another example, the first segment and the second segment may be separated by at least 10% of the radial area of the ostomy wafer or a layer thereof. Further, in yet another example still, the first segment and the second segment may be separated by at least 15% of the radial area of the ostomy wafer or a layer thereof.

In some embodiments, the first segment and the second segment of the ostomy wafers of the present disclosure may be separated by at least 20% of the radial area of the ostomy wafer or a layer thereof. Additionally, in some embodiments, the first segment and the second segment may be separated by at least 25% of the radial area of the ostomy wafer or a layer thereof. In some embodiments still, the first segment and the second segment may be separated by at least 30% of the radial area of the ostomy wafer or a layer thereof. In some embodiments yet still, the first segment and the second segment may be separated by at least 35% of the radial area of the ostomy wafer or a layer thereof. Further, in some embodiments, the first segment and the second segment may be separated by at least 40% of the radial area of the ostomy wafer or a layer thereof. Further, in some embodiments still, the first segment and second segment may be separated by at least 45% of the radial area of the ostomy wafer or a layer thereof. Finally, in some embodiments, the first segment and the second segment may be separated by at least 50% of the radial area of the ostomy wafer or a layer thereof.

Stoma Channel Built-In Structures

In some embodiments, the stoma channel (e.g., the annular opening in the wafer) has at least one built-in structure (e.g., any one or more of the features 910, 930, 950) to enhance the seal established between the ostomy wafer and the stoma. It should be appreciated that the stoma channel built-in structures contemplated herein are generally designed for use with a stoma and are capable of receiving, and/or coming into contact with, internal tissue that may be positioned in the stoma channel when the ostomy wafer is pushed against the stoma. As such, features (e.g., macro and micro shapes) of one or more walls that define the stoma channel of each ostomy wafer of the present disclosure provide a customized seal around an individual's stoma.

Such customization makes the seal more effective and increases leakage resistance. Additionally, such customization provides greater comfort to the particular user. Furthermore, in some embodiments, the built-in structures of the ostomy wafers disclosed herein facilitate quick and simple application (and removal) of the ostomy wafers, thereby reducing user application time, training time, and learning curves. In one example, built-in structures disclosed herein are macroscopic. In another example, built-in structures disclosed herein are microscopic. In yet another example, ostomy wafers disclosed herein include a combination of microscopic and macroscopic built-in structures.

In the illustrative embodiments, the built-in structures 910 shown in FIG. 9A are embodied as, or otherwise include, angled and/or tapered surfaces 912, 914. In some embodiments, the surfaces 912, 914 may define, or otherwise incorporate, one or more angled fins 932 defining notches 934 therebetween, which are depicted in FIG. 9A and which may be embodied as, or otherwise included in, the built-in structures 930. In any case, in some embodiments, each angled fin 932 and/or each notch 934 may have a height H (shown in FIG. 9B) of about 0.01 mm to about 10 mm. The height H may be the dimension perpendicular to a length L of the stoma channel. As shown in FIG. 9B, each angled fin 932 may have a width W1 measured with respect to a horizontal line 940 that is from 0.01 mm to 10 mm and a width W2 measured with respect to the line 940 that is from 0.01 mm to 20 mm. Additionally, as shown in FIG. 9B, each angled fin 932 may extend at an angle A relative to the line 940 that is from 0° to 60° and at an angle B relative to the line 940 that is from and angle B is 0-90°.

In some embodiments, built-in structures disclosed herein may define spring-like or accordion-like structures (e.g., the built-in structures 930, 950). Additionally, in some embodiments, built-in structures disclosed herein may allow the ostomy wafer to clamp onto a protruding stoma. In some embodiments still, built-in structures disclosed herein may prevent the ostomy wafer from dislodging from the stoma. In some embodiments yet still, built-in structures disclosed herein may have a spring/rebound property that controls deformation with a predetermined or reference rebound force. It should be appreciated that the built-in structures contemplated by the present disclosure may prevent, or substantially resist, a stoma from slipping out or pulling out of the stoma channel. Additionally, the built-in structures disclosed herein may provide frictional interference between the stoma channel and the stoma, thereby facilitating securement of the ostomy wafer to the stoma.

In some embodiments, ostomy wafers disclosed herein include built-in structures (e.g., the structures 930) located on the inner wall(s) defining the stoma channel. Additionally, in some embodiments, the built-in structures disclosed located on the inner surface of the stoma channel are tapered (e.g., the structures 910) or jagged (e.g., the structures 930), which prevent or resist detachment of the ostomy wafer from the protruding stoma. In some embodiments still, the built-in structures disclosed herein provide internal structures (e.g., the built-in structures 950 within the stoma channel wall(s) 952) that provide deformation and malleability without gripping and/or directly contacting the stoma.

In some embodiments, built-in structures disclosed herein may be described as pliable, flexible, semi-rigid, or a combination thereof. In other embodiments, however, built-in structures disclosed herein may be rigid or inflexible.

The ostomy wafers of the present disclosure include stoma channels of various shapes. In one example, the stoma channel is cylindrical. In another example, the stoma channel is tapered or funnel-shaped. In yet another example, the stoma channel has a smooth, continuous, or uninterrupted inner surface. In another example yet still, the stoma channel has a jagged or stepped inner surface.

In some embodiments, the stoma channel of the ostomy wafer and areas adjacent thereto may include moldable adhesive technologies. Those adhering features may reduce the number of steps typically required to seal an ostomy wafer to the skin and the stoma of a particular patient. For example, no scissors may be required to cut/tailor the stoma channel to the skin and the stoma of the patient, and there is may be no need for additional pastes or adhesives to fill in the contours/built-in structures of the ostomy wafer. Therefore, the ostomy wafers disclosed herein may offer easier and simpler application (and removal) for nurses and patients.

Wafer Layers

The ostomy wafers of the present disclosure include at least one wafer layer, and, in some embodiments, the ostomy wafers disclosed herein include multiple wafer layers. The layers may be selected from, or may otherwise incorporate, molds, adhesives, seals, barriers, or the like. Non-limiting examples of materials that may be included in layers of the ostomy wafers described herein are adhesives, composites, foams, gels, rubbers, plastics, fabrics, and combinations thereof. Generally, ostomy wafers disclosed herein include an external layer and a convex layer. It should be appreciated that each of the external layer and/or the internal layer may function as, or otherwise incorporate, an adhesive or an effective barrier against effluent leakage, at least in some embodiments. However, in other embodiments, the ostomy wafers disclosed herein include a single layer (e.g., the convex layer) that is adapted for use with other devices or on its own. In some embodiments, the external layer is ring-shaped and substantially planar relative to the convex layer. Typically, the convex layer has a three-dimensional ring shape that facilitates entry into, and fitting/molding to, a flush or retracted stoma. In some embodiments, the outer diameter of the external layer is greater than the outer diameter of the convex layer, and the convex layer is thicker than the external layer.

In some embodiments, ostomy wafers disclosed herein include an external layer. In such embodiments, the external layer is typically the outermost (i.e., distal to the individual or user) layer of the ostomy wafer, and typically, the external layer does not extend into the stoma or internally beyond the stoma when applied to the user. In some embodiments, the external layer includes a single layer. In other embodiments, however, the external layer includes a multilayer construction (e.g., multiple layers of material or a multi-laminate construction). In one example, the external layer includes a material selected from, but not limited to, hydrocolloid adhesives (such as Stomahesive, Durahesive, Modified Stomahesive, Stomahesive Seal, Duoderm, or Coloplasts Brava strips, for example), silicone, acrylics, cyanoacrylate (such as Liquiband, for example), rubbers, foams, cellulose, polyurethanes, polyethylenes, polyvinyl chlorides, ethylenevinyl acetates, polypropylenes, polytetrafluorethylenes, and polyisobutylenes. In some embodiments, the external layer may include Trilam (SH/DH) that has a Stomahesive seal or a Durahesive seal.

In some embodiments, ostomy wafers disclosed herein include a convex layer. The convex layer may be relatively cylindrical, funnel-shaped, and/or bowl-shaped, with a rim (e.g., the rims 116, 216, 316, 416 shown in respective FIGS. 1-4) that is in contact with the external layer. The opening (e.g., the openings 118, 218, 318, 418) of the convex layer through which effluent flows is generally positioned at/near the base of the bowl, opposite the mouth/rim. It should be appreciated that the convex layer should have appropriate dimensions for positioning into, around, or against a flush or retracted stoma. In one example, with regards to a flush stoma, the opening of the convex layer may be sized to fit around internal tissue such that the convex exterior rim of the "bowl" contacts the peristomal skin around the internal tissue and minimally extends beyond the surface of the skin surrounding the stoma. In the example of a retracted stoma, the convex layer may have a relatively shallow bowl depth and be wide enough to leave little or no space between the peristomal skin and the exterior rim and/or sides of the convex layer.

In some embodiments, the depth of the convex layer bowl may be between about half of a centimeter and about ten centimeters. Additionally, in some embodiments, the width of the bowl may be between about two centimeters and about ten centimeters. The convex layer, as well as additional components of the ostomy wafers disclosed herein, may be manufactured by use of compression molds that apply heat for adhesive molding, at least in some embodiments. In one example, the total volume of the bowl may range from 20,000 $mm^3$ to 800,000 $mm^3$. In another example, the total volume of the bowl may range from 20,000 $mm^3$ to 100,000 $mm^3$.

Figure 4:
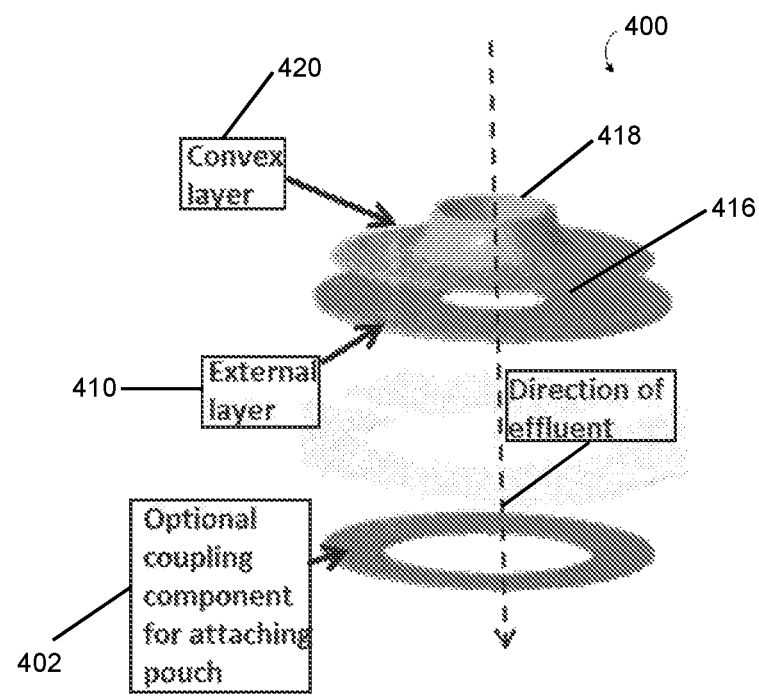
FIG. 4 illustrates an exploded view of one embodiment of a tapered ostomy wafer.

In some embodiments, convex layers disclosed herein are relatively funnel-shaped (e.g., the convex layer 420 in FIG. 4) instead of being relatively bowl-shaped (e.g., the convex layer 320 in FIG. 4). Funnel-shaped convex layers may be formed or sculpted from an adhesive material, at least in some embodiments. Additionally, in some embodiments, the adhesive material may be a moldable adhesive. In some embodiments still, the funnel-shaped convex layer may be formed or sculpted from a rigid or semi-rigid material. Non-limiting examples of rigid or semi-rigid materials include hydrocolloid adhesives (e.g., Stomahesive, Durahesive, Modified Stomahesive, Stomahesive Seal, Duoderm, or Coloplasts Brava strips), silicone, acrylics, cyanoacrylate (e.g., Liquiband), rubbers, foams, cellulose, polyurethanes, polyethylenes, polyvinyl chlorides, ethylenevinyl acetates, polypropylenes, polytetrafluorethylenes, and polyisobutylenes. In other embodiments, the funnel-shaped convex layer may not have an adhesive property. In such embodiments, the convex layer may be used with an internal layer that has an adhesive property to form a seal against the stoma. The internal layer or funnel-shaped convex layer may be able to absorb effluent as well, at least in some embodiments.

In some embodiments, convex layers of the ostomy wafers disclosed herein are constructed to provide convexity, support, and flexibility. In one example, the convex layer is made from ethylene vinyl acetate (EVA), a material which may be "rubber-like" in softness and flexibility, among other properties. The convex layer may include, but is not limited to, one or more rigid or semi-rigid plastics, such as polypropylene, polystyrene, or polyethylene (polyethylene-vinyl acetate), for example. The thickness of convex layers disclosed herein may range from about 22 mm (⅞") to about 45 mm (1¾") in size to increase suitability for use with retracted stomas, at least in some embodiments.

In some embodiments, the convex layer includes a skin barrier. The skin barrier may comprise a ring formed from, or in the form of, a mold. The mold may be flexible or pliable, at least in some embodiments. The convex layer and/or skin barrier may include an adhesive that is embodied as, or otherwise includes, a stoma adhesive. The stoma adhesive may provide a barrier or seal against effluent to ensure a single-directional flow through the opening of the convex layer (see the effluent flow arrows in FIGS. 1 and 2). Thus, the convex layer may be used alone with a pouch and provide adherence to the subject, as well as an effective barrier against leakage. In one embodiment, the skin barrier is a moldable adhesive that is breathable and/or moisture-absorbing. By way of non-limiting example, the skin barrier may be selected from Stomahesive Seal (ConvaTec), Brava Moldable adhesive Ring (Coloplast), Eakin Cohesive Seal (ConvaTec), Adapt Barrier Ring (Hollister), SecuPlast Mouldable Seal (Salts), and Siltac (Trio).

The skin barriers contemplated by the present disclosure are adapted to fill in and/or be received in cavities/folds in the intact skin around the stoma to protect the underlying skin from contact with bodily fluids. In some embodiments, the skin barriers may be made from pectin-based, hydrocolloid-type ingredients, mineral oils, plasticisers, tackifiers, and elastomers, with varying compositions. In some embodiments, the convex layer may include a single layer. Additionally, in some embodiments, the convex layer includes a multi-layer or multi-laminate material and/or multiple layers of material. The convex layer may include a material selected from one or more of the following: Eakin Cohesive Seal (ConvaTec), Brava Mouldable Ring (Coloplast), Dansac Seal (Dansac), Adapt Barrier Ring (Hollister), SecuPlast Mouldable Seal (Salts), and Siltac (Trio). The convex layer may comprise a material selected from Stomahesive seal, at least in some embodiments.

In some embodiments, the ostomy wafers disclosed herein include an internal layer that at least partially covers (ranging from about 30% to about 100%) the convex exterior surface of the convex layer and includes a stoma adhesive on a stoma-facing side of the internal layer. As such, the internal layer may adhere to flush or retracted skin of the flush or retracted stoma, thereby securing the ostomy wafer to the ostomate. The internal layer may include a material selected from one or more of the following: Eakin Cohesive Seal (ConvaTec), Brava Mouldable Rings (Coloplast), Adapt Barrier Rings (Hollister) Dansac Seal (Dansac), SecuPlast Mouldable Seal (Salts), and Siltac (Trio). The internal layer may include Stomahesive seal and/or Stomahesive paste, at least in some embodiments.

In some embodiments, the ostomy wafers disclosed herein include one or more additional layers having adhesive, at least in some embodiment. In other embodiments, the one or more additional layers may not include adhesive. The one or more additional layers may include a material selected from adhesive, laminate, foam, gel, rubber, fabric, plastic, and combinations thereof. Other ingredients may include, but are not limited to, Sodium Carboxymethylcellulose, Thixcin, Gelatin, and Pectin, for example.

The one or more additional layers may contribute to the flexibility or moldable adhesive character of the ostomy wafer. The one or more additional layers may also allow the ostomy wafer to have properties tailored to the needs of a particular patient demographic. As a non-limiting example, these may include thickness variations (from about 0.5 mm to about 40 mm), shape variations (such as circular, polygonal, or crescent shapes, for example), profile variations (constant profile or wedge profile), or surface features (such as ridges, channels, or valleys, for example).

The additional layers may be continuous or discontinuous around the periphery of the ostomy wafer. It should be appreciated that the ostomy wafers, devices, and methods disclosed herein generally avoid the use of rigid, hard materials to form the convex exterior of the convex layer.

Accordingly, the ostomy wafers, devices, and methods disclosed herein provide malleability and flexibility while at the same time delivering a secure seal to resist leakage.

As exemplified in FIG. 1, ostomy wafers disclosed herein may include two layers having two different types of adhesive (e.g., the layer 120 and the layer 130). The wafer may also include an external layer (e.g., the layer 110). One exemplary embodiment includes Trilam as the internal layer (e.g., the internal layer 130) which may overlap the convex layer (e.g., the convex layer 120). Other exemplary adhesives include hydrocolloid adhesives such as Durahesive, Stomahesive, Modified Stomahesive, Stomahesive Seal, and Duoderm, for example. The convex layer may be embodied as, or otherwise include, an adhesive barrier seal, which may also be referred to as a stoma gasket or barrier ring. One exemplary embodiment includes the use of a Stomahesive seal. Other exemplary adhesives include hydrocolloid adhesives such as Durahesive, Stomahesive, Modified Stomahesive, Stomahesive Seal, and Duoderm, for example.

In embodiments in which the convex layer has, or acts as, an adhesive barrier seal, the convex layer may provide a malleable core of the wafer to facilitate conformance and/or molding of the wafer to the stoma, protruding ileum, and surrounding skin upon compression of the wafer to the abdomen. In some embodiments, a double-layered adhesive may additionally form a moldable adhesive "original" shape that can adapt to the external environment and form an "adapted shape" different from the original shape. The adhesive may include three dimensional rebounding technology consisting of a tri-laminate material that is able to return to its original shape, at least in some embodiments. In other embodiments, the material may undergo plastic deformation under temperature change and/or pressure to adapt to a new shape. In some embodiments, the soft construction of the convex layer may be characterized as quasi-fluid. In other words, due to the avoidance of relatively hard materials in the construction of the convex layer, the ostomy wafers disclosed herein may be more malleable than other wafer configurations, while still enhancing the comfort of the user and ensuring a secure seal to resist leakage.

Figure 2:
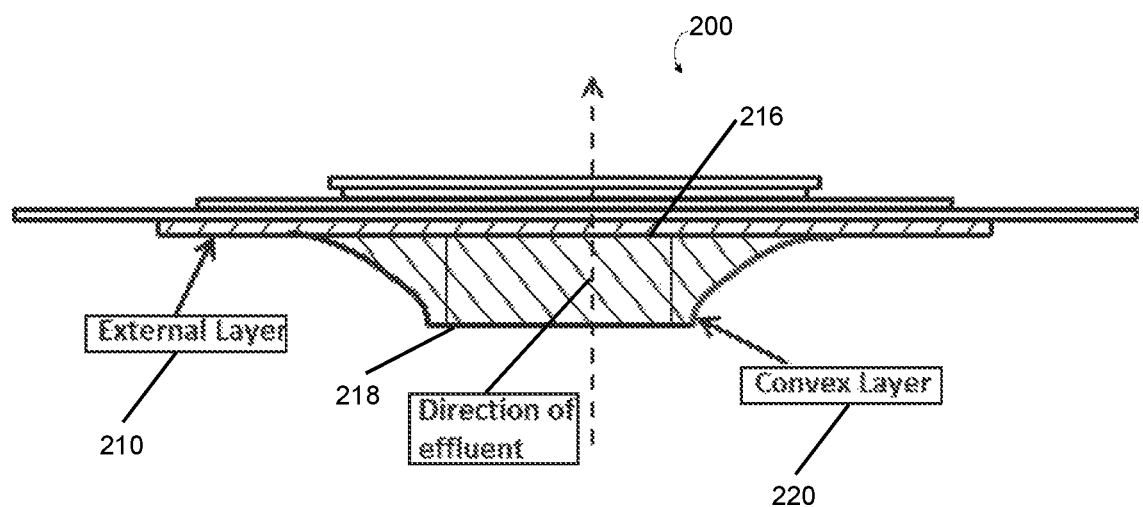
FIG. 2 illustrates a cross-sectional view of one embodiment of a tapered ostomy wafer.
Figure 3:
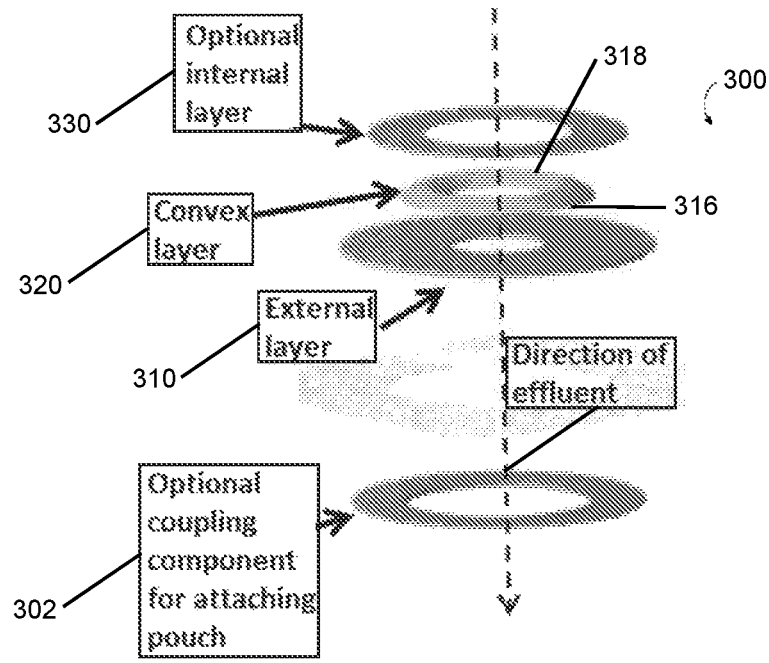
FIG. 3 illustrates an exploded view of one embodiment of an ostomy wafer.

As exemplified in FIG. 2, ostomy wafers disclosed herein may include two layers (e.g., the layers 210, 220) that form a tapered wafer having a relatively funneled shape (i.e., in comparison the wafer depicted in FIG. 1). The tapered wafer may be particularly useful for flush or retracted stomas, at least in some embodiments. The tapered adhesive of the convex layer (e.g., the convex layer 220) may permit an effective seal of the ostomy wafer around the base of the ileum or perimeter of the stoma. By placing the top or rim of the tapered convex layer around the stoma edge, the wafer may be molded to the stoma, at least in some embodiments. The tapered adhesive may be manually molded by the user to the stoma and the peristomal skin upon attachment of the adhesive thereto to minimize leakage and create a secure fit.

The external layer (e.g., the external layer 210) may provide a structural base for the ostomy wafer while the convex layer provides a softer, more pliable adhesive, thereby allowing the user to achieve an effective seal around the base of the ileum and/or the perimeter of the stoma. The external layer may include a multi-laminate adhesive having a molding adhesive, a central film, and a body side, at least in some embodiments. The external layer may include Trilam (SH/DH). The convex layer may include an adhesive selected from, but not limited to, Stomahesive, Durahesive, Modified Stomahesive, and Stomahesive Seal.

In some embodiments, the ostomy wafers disclosed herein include a flange, a collar, or a baseplate. Additionally, in some instances, the ostomy wafers disclosed herein include a flange, which may be a feature that allows coupling to a complementary component. In some embodiments still, the flange may extend radially outward from the rest of the ostomy wafer or a layer thereof. In some embodiments yet still, the ostomy wafers disclosed herein may include an extension to the adhesive layer (e.g., a collar) which attaches to the skin. The collar may be made of fabric, at least in some embodiments. A flange or tab may extend radially outward from the ostomy wafer at a single location, whereas a collar may extend radially outward from the ostomy wafer around the outer perimeter of the device.

The flange or collar may be attached to the external layer and/or the convex layer. In some embodiments, the flange or collar may include additional adhesive for further securing the ostomy wafer to the ostomate and/or sealing the ostomy wafer to the ostomate to resist leakage. Common substances, devices, and/or methods may be employed to securely mate and seal a flange to a stoma, such as applying an adhesive substance (e.g., a paste) around the stoma, at the base of the ileum, and/or at the opening of the ostomy wafer/baseplate as filler for skin folds, uneven skin surfaces, and scars, for example. Other methods may involve using silicone gel to fill uneven skin surfaces, applying the gel directly around the stoma, and applying a wafer/baseplate directly onto the gel. According to such methods, the gel may cure underneath the wafer/baseplate during normal wear time. Non-limiting examples of pastes include ConvaTec's Stomahesive paste, Adapt Paste (Hollister), Brava Paste (Coloplast), Securiti-T Stoma Paste (Genairex), MicroHesive Stoma Paste (Cymed), and Osto Stoma Paste (Montreal Osto). Gels include, but are not limited to, Silicone Gel (Trio), and Osto Paste (Stoma-Tech). Additionally, in some embodiments, ingredients of the pastes/gels may include, but are not limited to, Sodium Carboxymethylcellulose, Thixcin, Gelatin, and Pectin.

Ostomy Wafer Properties

The ostomy wafers of the present disclosure have various physical properties. In some embodiments, various regions or segments of ostomy wafers disclosed herein possess varying physical properties. Furthermore, ostomy wafers disclosed herein, and portions thereof, may have various rheological properties. In some embodiments, the rheological properties of ostomy wafers disclosed herein may be supported or enhanced by any one of the layers, structures, or features described herein. Additionally, in some embodiments, layers, structures, or features of the ostomy wafers disclosed herein provide structural rigidity, and thereby establish boundary conditions of the wafers.

The gross diameters of the wafers contemplated by the present disclosure range up to about 200 mm, and the heights of the ostomy wafers disclosed herein range from about 3 mm to about 30 mm. In some embodiments, ostomy wafers disclosed herein range in average size from about 10 mm to about 100 mm in diameter. The ostomy wafers disclosed herein may function to direct viscous internal fluid flow, at least in some embodiments. The ostomy wafers of the present disclosure may facilitate the use of dynamic fluid viscosities as low as about $0.28 \times 10^{-3}$ Pa·s$^{-1}$, and as high as about $1 \times 10^8$ Pa·s$^{-1}$.

The total height of ostomy wafers disclosed herein is more than about 5 mm, more than about 10 mm, or more than about 20 mm, at least in some embodiments. Additionally, in some embodiments, the wafers may have total heights of about 3 mm to about 30 mm. In some embodiments still, the wafers may have total heights of no more than about 50 mm. In some embodiments yet still, the outer diameter of the wafers may range from about 5 mm to about 150 mm. Further, in some embodiments, the outer diameter may range from about 10 mm to about 100 mm. Further, in some embodiments still, the outer diameters may range from about 20 mm to about 200 mm. Further, in some embodiments yet still, the outer diameters may range from about 100 mm to about 200 mm. Finally, in some embodiments, a wafer with an outer diameter greater than 200 mm may be particularly desirable.

Ostomy wafers of the present disclosure, or portions thereof, may have a stiffness that ranges from about 0.1 N/mm to about 300 N/mm, at least in some embodiments. Additionally, in some embodiments, the wafers disclosed herein may have a stiffness that ranges from about 0.15 N/mm to about 200 N/mm. Finally, in some embodiments, the wafers disclosed herein may have a stiffness that ranges from about 0.5 N/mm to about 150 N/mm.

Ostomy wafers of the present disclosure, or portions thereof, may securely fill and/or seal voids (e.g., creases, folds, or pockets) in the skin of the subject. In some embodiments, each void may be greater than about 0.01 $mm^3$, about 0.02 $mm^3$, about 0.05 $mm^3$, or about 0.1 $mm^3$. In other embodiments, each void may be greater than about 0.02 $mm^3$.

In some embodiments, ostomy wafers disclosed herein, and portions thereof, include at least one material having a tensile strength of about 0.1 $N \cdot cm^{-2}$ to about 20 $N \cdot cm^{-2}$. Additionally, in some embodiments, ostomy wafers disclosed herein, and portions thereof, include at least one material having a tensile strength of about 0.5 $N \cdot cm^{-2}$ to about 15 $N \cdot cm^{-2}$. In some embodiments still, ostomy wafers disclosed herein, and portions thereof, include at least one material with a tensile strength of about 1 $N \cdot cm^{-2}$ to about 10 $N \cdot cm^{-2}$.

In some embodiments, ostomy wafers disclosed herein, and portions thereof, have a maximum elongation property of up to 100%. Additionally, in some embodiments, ostomy wafers disclosed herein, and portions thereof, have a maximum elongation property of up to 200%. In some embodiments still, ostomy wafers disclosed herein, and portions thereof, have a maximum elongation property of up to 300%. In some embodiments yet still, ostomy wafers disclosed herein, and portions thereof, have a maximum elongation property of up to 400%. Further, in some embodiments, ostomy wafers disclosed herein, and portions thereof, have a maximum elongation property of up to 500%. Further, in some embodiments still, ostomy wafers disclosed herein, and portions thereof, have a maximum elongation property of up to 800%. Further, in some embodiments yet still, ostomy wafers disclosed herein, and portions thereof, have a maximum elongation property of up to 1000%.

In some embodiments, the convex layers of the ostomy devices of the present disclosure may have a tapered or graduated shape. Additionally, in some embodiments, the convex layer may have a cylindrical shape or cylindrical characteristic. In other embodiments still, the convex layer may have a proximal end or proximal opening that is positioned in the flush or retracted stoma and a distal end or distal opening that extends away from, and is positioned outside of, the stoma. Regardless, the convex layer may have a threshold thickness that is about 30 mm, about 40 mm, about 45 mm, about 50 mm, about 55 mm, or about 60 mm, at least in some embodiments. In one embodiment, the threshold thickness may be about 45 mm. It should be appreciated that the thickness of the wall of the convex layer may be greater at the proximal end or proximal opening compared with the thickness of the wall at the distal end or the distal opening. The ratio of the distal:proximal may range from 1:1 (e.g., cylinder form) up to 1:0.01 (e.g., tapered form). Thus, the distal end or distal opening of the convex layer may be sized to conform easily to an individual's unique contours.

As exemplified in FIG. 2, the convex layer (e.g., the layer 220) of ostomy wafers disclosed herein may be tapered to provide an effective seal around the base of the ileum or the perimeter of the stoma, at least in some embodiments. Due to the smaller thickness of the convex layer toward the top/distal end) (i.e., as compared to the thickness of the convex layer toward the bottom/proximal end), the convex layer may have improved malleability, which may enhance conformance to each individual's unique characteristics. Additionally, in some embodiments, a stomal taper may allow an interference fit to be achieved for many different stomal sizes from a single manufactured profile. For a given application force, the taper may increase the stress experienced by the ostomy wafer material and the pressure exerted on the tissue surrounding the stoma by the ostomy wafer. Consequently, the ostomy wafer may conform to the user with greater ease and improve the protrusion of an inverted or flush stoma, which may be particularly useful for debilitated patients. In some embodiments, ostomy wafers disclosed herein may begin deformation with application forces as low as about 0.1 N, about 0.2 N, about 0.5 N, or about 1 N.

Adhesives

The illustrative ostomy wafers of the present disclosure generally include adhesives or adhesive layers. As used herein, the term "adhesive" refers to layers, fabrics, strips, laminates, barriers, gels, pastes, hydrocolloids, glues, or the like that may be used to promote adherence of the ostomy wafer to the ostomate and/or promote a seal between the ostomy wafer and the ostomate to resist undesirable leakage of effluent. The adhesive may include a sealing substance that promotes a seal between the ostomy wafer and the stoma/ostomate, at least in some embodiments. It should be appreciated, however, that in some embodiments, inclusion of an adhesive in the ostomy wafer may be unnecessary. In some embodiments, kits and/or methods contemplated by the present disclosure may include an adhesive or involve the use of an adhesive, and the adhesive (e.g., an adhesive paste) may be applied to the ostomy wafer to effectively eliminate gaps between the stoma and the ostomy wafer in use of the ostomy wafer.

In some embodiments, the convex layers of the ostomy wafers and methods disclosed herein may include a stoma adhesive that adheres the convex layer to the flush or retracted skin of the flush or retracted stoma to provide additional means for securing and/or sealing the ostomy wafer to the ostomate. Additionally, in other embodiments, the width of the distal opening may be greater than the width of the proximal opening. In such embodiments, the width disparity between the distal opening and the proximal opening may facilitate application of the wafer to a particular patient (e.g., due to the greater aperture size of the proximal opening to locate over the stoma), which may be particularly advantageous to visually impaired or dexterity impaired patients.

Adhesives may also be used to promote adherence of an ostomy pouch to the ostomy wafer. The adhesives disclosed herein may provide adhesion for a variety of skin conditions, as well as security and comfort for the patient. In some embodiments, to ensure the skin barrier adheres to moist/dry skin, hydrocolloids may be used. Additionally, in some embodiments, the adhesives, such as barriers, seals, strips, laminates, or fabrics, for example, may include a release liner designed for removal prior to use. In other embodiments, however, the adhesives may not include a release liner. In such embodiments, the adhesive quality of the adhesive may be present only when the adhesive makes contact with a liquid, gel, effluent, skin, heat, or a combination thereof.

The adhesives may have an adhering, sealing, or molding quality that is activated and/or promoted by heat and/or contact with effluent. By way of non-limiting example, sealing materials of the adhesives may include Eakin Cohesive Seal (ConvaTec), Brava Mouldable Rings (Coloplast), Dansac Seal (Dansac), Adapt Barrier Rings (Hollister), SecuPlast Mouldable Seal (Salts), and Siltac (Trio). Sealing pastes contemplated by the present disclosure include, but are not limited to, Stomahesive Paste (ConvaTec), Adapt Paste (Hollister), Brava Paste (Coloplast), Securiti-T Stoma Paste (Genairex), MicroHesive Stoma Paste (Cymed), and Osto Stoma Paste (Montreal Osto). By way of non-limiting example, gel sealants contemplated herein include Silicone Gel (Trio) and Osto Paste (Stoma-Tech). Other ingredients of the adhesives may include, but are not limited to, Polyisobutylene, Gelatin, Pectin, Thixcin, Sodium Carboxymethylcellulose (Sodium CMC), and Hydroxyethyl Cellulose, at least in some embodiments.

In an exemplary embodiment, the ostomy wafers disclosed herein may include ConvaTec Moldable adhesive Technology (CMT), which improves the fit between skin barriers and stomas. In one example, Durahesive technology used in CMT may help to protect the skin from caustic effluent. Durahesive technology combines the ingredients used in stomahesive technology in a different ratio to produce a moisture-absorbing adhesive. In some embodiments, the inclusion of Durahesive technology in convex wafers may ensure easy one-piece removal (i.e., due to higher cohesive strength) that is gentle on the surrounding skin. Durahesive polymers may swell within an elastic matrix to create a seal around the stoma site.

Durahesive polymers may swell or "turtleneck" in response to coming in contact with liquid effluent to improve the seal around the stoma. The expansion and contraction around the stoma in use of such polymers may provide a barrier that remains snug and secure during period of wear. It should be appreciated that ensuring a good seal around the stoma minimizes the risk of effluent leaking under the skin barrier, and that reducing such leakage resists the development of peristomal skin complications.

The ostomy wafers disclosed herein, and components thereof, may include an adhesive selected from various adhesives, such as, but not limited to, Stomahesive/Durahesive, Trilaminate, and Stomahesive Seal, for example. The formulation of the adhesives may be altered to deliver a desired attribute to the user (e.g. comfort, flexibility, size, breathability, etc.), at least in some embodiments. To improve the elasticity of the adhesive, an additive (e.g., styrene-isoprene-styrene (SIS) rubber, isobutylene) may be utilized. In some embodiments, oils may be added to enhance pliability and tack.

The adhesives disclosed herein may include a mucoadhesive. The mucoadhesive may be particularly helpful to maintain sufficient adhesion under wet conditions, among other conditions. In some embodiments, the mucoadhesive of the present disclosure includes a polymer having functional groups selected to provide adhesion to the skin and the stoma. In one example, the functional groups are selected from a group consisting of thiols, acids and their salts, iminothiolanes, thioalkylamidines, catechols, amino acids, dihydroxy substituted aromatic groups, and combinations thereof. Additionally, in one example, the polymer is a biocompatible polymer made from natural or synthetic polymer selected from a group consisting of polyacrylates, polyakylmethacrylates, polyphenylmethacrylate, polyanhydrides, styrenic block copolymers, polyamides, polyesters, polyvinyl ethers, polyvinyl esters, sulfonated polymers, polyolefins, silicones, polyvinylpyrrolidones, polyvinylacetate and its copolymers, polyvinyl alcohol, polyurethanes, polyethers, copolymers of maleic anhydride, polysaccharides, polypeptides, gelatin, alginates, gums, starch, chitosan, pectin, and combinations thereof. Further, in some embodiments, the mucoadhesive may contain other components such as hydrophobic polymers, hydrophilic polymers, amphiphilic polymers, tackifiers, resins, plasticizers, hydrocolloids, inorganic and organic particulate fillers, antioxidants, stabilisers, organic and inorganic pigments, lubricious additives, and combinations thereof.

The adhesives may include a pressure sensitive adhesive having one or more amphiphilic copolymers of polydimethylsiloxane, at least in some embodiments. In such embodiments, the copolymer may be prepared using a polydimethylsiloxane or polymethylhydrogensiloxane macroinitiator and at least one reactive hydrophilic or amphiphilic monomer, oligomer, macromere, or combinations thereof. In some embodiments, the reactive hydrophilic or amphiphilic monomer may be selected from a group consisting of N-vinyl caprolactams, vinyl esters, vinyl ethers, unsaturated acids or anhydrides and their salts, acrylates, methacrylates, acrylamides, methacrylamides, N-alkyl acrylamides, cyanate esters, hydroxy-alkyl acrylamides, glycidyl esters, glycidyl ethers, allyl monomers, and combinations thereof.

Ostomy Devices

Ostomy devices of the present disclosure include an ostomy pouch and any one of the ostomy wafers disclosed herein. In some embodiments, the ostomy device may include one or more coupling components (e.g., the components 302, 402 shown in FIGS. 3 and 4) configured for interaction with the ostomy pouch and/or the ostomy wafer to operatively couple the ostomy pouch and the ostomy wafer in use thereof.

The ostomy wafers of the present disclosure may include one or more coupling components to couple or adhere the ostomy wafer to an ostomy pouch. The coupling component(s) may be attached to any ostomy wafer disclosed herein. In some embodiments, the coupling component(s) may be included in the ostomy wafer or any layer thereof. In any case, it should be appreciated that the coupling component(s) are adapted to mechanically connect the ostomy wafer to the ostomy pouch, such as via adhesion by an adhesive layer applied to, coupled to, or otherwise incorporated into, the ostomy wafer and/or the ostomy pouch, or by interaction with one or more additional components. Of course, in other embodiments, the ostomy wafer may not include coupling component(s). In such embodiments, the ostomy wafer may contact the pouch directly or may contact a coupling feature of the pouch.

In some embodiments, the coupling component(s) may include, be embodied as, or otherwise provide, a limited motion connection between the ostomy wafer and the ostomy pouch that permits relative displacement between substantially the entire ostomy wafer and the entrance aperture of the ostomy pouch. In such embodiments, the limited motion connection may guide relative displacement between the wafer and the pouch along a limited motion locus. More specifically, in some embodiments, the limited motion connection may guide movement of the wafer relative to the pouch (or vice versa) between an operative position and an access position. In the operative position, the ostomy wafer may be superposed around the entrance aperture of the ostomy pouch. Additionally, in the operative position, an adaptable region of the ostomy wafer may be shrouded by the ostomy pouch on the non-body-facing side and the wafer and pouch may be fixed to one another with a fixation coupling. In the access position, access is provided to the adaptable region from the non-body-facing side.

The coupling component(s) contemplated herein may guide alignment of, or movement between, the ostomy wafer and the ostomy pouch to the operative position, thereby facilitating use for some users, such as elderly, non-dexterous, or visually impaired persons, for example. At the same time, the limited motion connection may permit relative displacement of substantially the entire ostomy wafer with respect to the entrance aperture as discussed above, thereby facilitating conformance of the ostomy wafer to the size and/or shape of the user's stoma, at least in some embodiments. In some embodiments, the limited motion connection may include an articulating link that defines the limited motion locus.

In some embodiments, the ostomy device may be provided as a one-piece component to enhance access thereto and avoid complications such as wholly or partly immovable ostomy wafers, for example. The ostomy wafer may be permanently attached to the ostomy pouch directly or indirectly via the coupling component(s) (which may be permanently attached to the ostomy pouch). For the purposes of the present disclosure, the term "permanently attached" (or like phrases) means that the pieces may be attached with sufficient force that separation of the pieces results in breakage or damage complicating reattachment without additional equipment. Of course, it should be apparent from the teachings of the present disclosure that the ability to displace the ostomy wafer relative to the entrance aperture of the ostomy pouch may permit easier adaptation of the ostomy wafer (e.g., by forming, cutting, or shaping the stomal aperture, or by fitting and/or shaping a separate sealing member at the stomal aperture) to the ostomy pouch.

In some embodiments, the ostomy device may be a two-piece ostomy device. The components of the two-piece device may be aligned without significantly reducing access to the ostomy wafer to facilitate adaption of the ostomy wafer to the size and/or shape of stoma. Additionally, the components may be positioned relative to one another without detracting from the ability to position the body-fitment component on the body before fixing the other component in the operative position with respect to the body fitment component. In some embodiments, the limited motion connection and the coupling component(s) may include releasable coupling portions.

Uses

While the devices (ostomy wafers and ostomy devices) disclosed herein are especially advantageous for the management of flush or retracted stomas, the devices disclosed herein may be used for protruding stomas as well. Generally, a protruding stoma is characterized by internal tissue (e.g., ileum) protruding from a surgical opening beyond the surface of surrounding external skin. Although a flush stoma may be described as having protruding internal tissue, the protruding tissue is surrounded by, and typically does not protrude beyond, the surrounding skin such that the distal end of the protruding internal tissue is flush with surrounding external and/or peristomal skin. A retracted stoma may be characterized by an absence of protruding internal tissue. In the case of a retracted stoma, the internal tissue does not protrude beyond the perimeter of the stoma or the skin surrounding the stoma.

The devices disclosed herein are adapted for use with a gastrointestinal stoma, at least in some embodiments. Additionally, in some embodiments, the devices disclosed herein may be used for managing a stoma created by an esophagostomy, a gastrostomy, a cholecystostomy, a choledochostomy, a cecostomy, a colostomy, a duodenostomy, an ileostomy, a jejunostomy, an appendicostomy, a tracheostomy, a urostomy, a nephrostomy, an ureterostomy, or a vesicostomy. In some embodiments still, the devices disclosed herein may be used with additional devices including, but not limited to, a shunt, a catheter, a plug, or a fecal management system.

In the case of a flush stoma, the ostomy wafers disclosed herein (e.g., the convex layers thereof) may be pressed into or against the stoma so that the internal tissue passes through the opening of the convex layer. In those embodiments, the opening of the convex layer may surround the internal tissue and the peristomal skin at least partially surrounds or buries the convex layer.

In the case of a retracted stoma, the convex layer of the ostomy wafers disclosed herein may be pressed into or against the stoma such that the convex layer is at least partially surrounded by, or buried in, the peristomal skin without the opening of the convex layer surrounding any internal tissue. Such positioning may provide a rebounding aspect to cause compression of the ostomy wafer (e.g., the convex layer) into gaps/contours in the patient's abdomen, at least in some embodiments.

In some embodiments, the ostomy wafers disclosed herein include an external layer having a body-contacting side and a convex layer that contacts or is in communication with the external layer and is sized to be positioned in a flush or retracted stoma. The external layer and the convex layer include concentric openings through which effluent flows in use of the ostomy wafer. In some embodiments, the ostomy wafers disclosed herein may be embodied as, or otherwise include, "layered adhesive wafers." The moldable convex layers of the layered adhesive wafers disclosed herein may be more pliable than other configurations of convex discs. The body-contacting side of the external layer may include a skin adhesive that adheres the external layer to external and/or peristomal skin around and/or adjacent to the flush or retracted stoma to secure the ostomy wafer to an individual or ostomate.

The ostomy wafers of the present disclosure may be used in combination with an ostomy pouch to manage a flush or retracted stoma as indicated above. In some embodiments, the ostomy wafer may be used with a plug that at least partially fills the stoma channel. Additionally, in some embodiments, the ostomy wafer may be used with an adhesive substance that promotes adherence of the ostomy wafer to the ostomate. The ostomy wafers disclosed herein may be used with heat for molding the ostomy wafer and/or promoting the adherent property of the additional adhesive, at least in some embodiments. In one example, at least a portion of the heat may be body heat produced by the user/ostomate. In another example, at least a portion of the heat may be externally provided heat.

Kits

The present disclosure contemplates kits that include any one of the ostomy wafers disclosed herein. In addition, the kits may include one or more components such as an ostomy pouch, an adhesive seal, an adhesive barrier, an adhesive strip, an adhesive fabric, an adhesive paste, and combinations thereof, for example. In some embodiments, the kits may include an adhesive selected from Adapt Paste (Hollister), Brava Paste (Coloplast), Securiti-T Stoma Paste (Genairex), MicroHesive Stoma Paste (Cymed), and Osto Stoma Paste (Montreal Osto). Additionally, in some embodiments, the kits may include gels such as Silicone Gel (Trio) or Osto Paste (Stoma-Tech), for example.

EXAMPLES

The examples and embodiments described herein are for illustrative purposes only and are not intended to limit the scope of the claims. It should be appreciated that various modifications or changes apparent to persons skilled in the art are within the spirit and purview of this application and scope of the appended claims.

Example 1: Application of a Convex Ostomy Wafer

An ostomate with a recessed stoma ensures that his/her hands and the skin surrounding the stoma are clean, dry, and free from any solvent or oily substances before applying the ostomy wafer. The ostomy wafer has an external layer and a convex layer that may be described as a funnel-shaped skin barrier (e.g., refer to the convex layer 420 shown in FIG. 4). The convey layer/skin barrier is made of a moldable adhesive such that the skin barrier is moldable to the stoma opening (i.e., the shape and size thereof) without needing scissors to adapt (e.g., to cut, tear, etc.) the ostomy wafer.

The first release liner is removed from the skin barrier and the opening of the skin barrier is centered over the stoma. The skin barrier is then applied against the skin around the stoma for 30 seconds while allowing the barrier to adapt/mold to the environment. When compressed against the abdomen, the moldable adhesive conforms to the contours of the ostomate to provide an effective, comfortable seal around the stoma. Thereafter, a second release liner is removed from the body-facing side of the external layer to reveal a skin adhesive. The body-facing side of the external layer is then also pressed to the skin surrounding the stoma to further secure the ostomy wafer to the ostomate. The ostomy wafer additionally includes a coupling component that is connected to an ostomy pouch. After use, the ostomy wafer is gently peeled from the body. Any residue can be removed from the skin by rolling and peeling, or by using Sensi-Care or Niltac Sting Free Adhesive Remover.

Example 2: Applying an Ostomy Wafer with Gaps or Grooves

An ostomate with a flush stoma (e.g., where the stoma entrance is relatively buried in a skin fold or crease) ensures that his/her hands and the skin surrounding the stoma are clean, dry, and free from any solvent or oily substances before applying the ostomy wafer. The ostomy wafer has an external layer and a convex layer that is a skin barrier made of a moldable adhesive. The ostomy wafer has at least one gap or groove in the ostomy wafer.

The ostomate folds or bends the skin barrier to deform the ostomy wafer, which defines a pointed region or tented region sized for receipt in a pocket or crease of the ostomate's skin or within a skin fold of the ostomate. Optionally, the ostomate, with aid from another person as needed, may push or lift skin burying or concealing the stoma away from the stoma to access the stoma in preparation for applying the ostomy wafer. The ostomate or other subject then applies the pointed or tented region to the revealed stoma and molds the skin barrier to the stoma opening (i.e., to the shape and size thereof) without using scissors to adapt the ostomy wafer to the stoma.

The first release liner is removed from the skin barrier. Thereafter, the opening of the skin barrier is centered over the stoma. The skin barrier is then applied against the skin around the stoma for 30 seconds while allowing the barrier to adapt/mold to the environment. When compressed against the abdomen, the moldable adhesive conforms to the contours of the ostomate to provide an effective, comfortable seal around the stoma. A second release liner is removed from the body-facing side of the external layer to reveal a skin adhesive. The body-facing side of the external layer is then pressed to the skin surrounding the stoma to further secure the ostomy wafer to the ostomate. The ostomy wafer additionally includes a coupling component that is connected to an ostomy pouch. Skin that was lifted or pushed away from the buried stoma is rested over the ostomy wafer. After use, the ostomy wafer is gently peeled from the body. Any residue can be removed from the skin by rolling and peeling, or by using Sensi-Care or Niltac Sting Free Adhesive Remover.

Example 3: Applying an Ostomy Wafer with Ridges

An ostomate with a recessed or flush stoma (e.g., that is accessible without moving skin away from the stoma) has creases in peristomal skin and surrounding skin on either side of the stoma parallel with their waistline. The ostomate ensures his/her hands and the skin surrounding the stoma are clean, dry, and free from any solvent or oily substances before applying the ostomy wafer. The ostomy wafer has an external layer and a convex layer that includes a funnel-shaped skin barrier made of a moldable adhesive. The convex layer also has twin ridges (e.g., see the ridges 710 shown in FIG. 7) that have a greater rigidity than the skin barrier.

The skin barrier is molded to the stoma opening (i.e., the shape and size thereof) without using scissors to adapt the ostomy wafer to the stoma. The first release liner is removed from the skin barrier. The opening of the skin barrier is centered over the stoma and the ridges are aligned with the creases in the skin. The skin barrier is applied against the skin around the stoma for 30 seconds while allowing the barrier to adapt/mold to the environment such that the ridges fill the skin creases. When compressed against the abdomen, the moldable adhesive conforms to the contours of the ostomate to provide an effective, comfortable seal around the stoma. A second release liner is removed from the body-facing side of the external layer to reveal a skin adhesive. The body-facing side of the external layer is then also pressed to the skin surrounding the stoma to further secure the ostomy wafer to the ostomate. The ostomy wafer additionally includes a coupling component that is connected to an ostomy pouch. After use, the ostomy wafer is gently peeled from the body. Any residue can be removed from the skin by rolling and peeling, or by using Sensi-Care or Niltac Sting Free Adhesive Remover.

Example 4: Applying an Ostomy Wafer with Stoma Channel Built-In Structures

An ostomate with a protruding stoma ensures his/her hands and the skin surrounding the stoma are clean, dry, and free from any solvent or oily substances before applying the ostomy wafer. The ostomy wafer has an external layer and a convex layer including a skin barrier that is made of a moldable adhesive. The convex layer has a stoma channel that is partially made of the moldable adhesive. The stoma channel is lined with angled fins which are directed toward the ostomate during use. The angled fins are made of a material similar to the moldable adhesive that gives them more rigidity than the moldable adhesive and allows them to at least partially retain their structure during molding of the convex layer.

The skin barrier is molded to the stoma opening (i.e., the shape and size thereof) without using scissors to adapt the ostomy wafer to the stoma. The first release liner is removed from the skin barrier. The opening of the skin barrier is centered over the stoma. The skin barrier is applied against the skin around the stoma for 30 seconds while allowing the barrier to adapt/mold to the environment. When compressed against the abdomen, the moldable adhesive conforms to the contours of the ostomate to provide an effective, comfortable seal around the stoma. A second release liner is removed from the body-facing side of the external layer to reveal a skin adhesive. The body-facing side of the external layer is then also pressed to the skin surrounding the stoma to further secure the ostomy wafer to the ostomate. The ostomy wafer additionally includes a coupling component that is connected to an ostomy pouch. The ostomate gives the resulting ostomy device a slight tug to ensure the stoma channel is secured to the protruding stoma via the angled fins. After use, the ostomy wafer is gently peeled from the body. Any residue can be removed from the skin by rolling and peeling, or by using Sensi-Care or Niltac Sting Free Adhesive Remover.

Example 5: Applying an Ostomy Wafer with Segments

An ostomate having a stoma with a nearby hernia ensures his/her hands and the skin surrounding the stoma are clean, dry, and free from any solvent or oily substances before applying the ostomy wafer. The ostomy wafer has an external layer and a convex layer including a skin barrier made of a moldable adhesive. The ostomy wafer has multiple gaps in the ostomy wafer (e.g., refer to the gaps 610 shown in FIG. 6).

The ostomate folds and bends the skin barrier between the several gaps to deform the ostomy wafer in a particular location to accommodate the nearby hernia. The skin barrier is molded to the stoma opening (i.e., the shape and size thereof), as well as the hernia, without using scissors to adapt the ostomy system. The first release liner is removed from the skin barrier. The opening of the skin barrier is centered over the stoma. The skin barrier is applied against the skin around the stoma for 30 seconds while allowing the barrier to adapt/mold to the environment. When compressed against the abdomen, the moldable adhesive conforms to the contours of the ostomate to provide an effective, comfortable seal around the stoma. A second release liner is removed from the body-facing side of the external layer to reveal a skin adhesive. The body-facing side of the external layer is then also pressed to the skin surrounding the stoma to further secure the ostomy wafer to the ostomate. The ostomy wafer additionally comprises a coupling component that is connected to an ostomy pouch. After use, the ostomy wafer is gently peeled from the body. Any residue can be removed from the skin by rolling and peeling, or by using Sensi-Care or Niltac Sting Free Adhesive Remover.

Example 6: Optimizing Fit and Dimension

The ostomy wafers disclosed herein may fit appropriately to each user. To ensure an appropriate fit, testing the coverage around the abdomen is important. The comfort of the user should be considered and evaluated before user trials. Comfort may be assessed with Ink testing and/or Flex testing (e.g., Zwick U.T.M). Testing leakage is also important. Minimal leakage is desired and can be tested by ISO 8670-2.

Flex Testing (TD-0409)

A Zwick Tensile testing machine and an appropriate load cell (for the sample to be tested) are provided. The stanchions of the test fixture are adjusted to the appropriate size for the wafer being tested. Before testing the wafer, the release liner is removed and the sample is placed centrally. The Flex Test Blade is lowered and a force is applied to flex the wafer by 8 mm for 0.1 seconds.

While the disclosure has been illustrated and described in detail in the foregoing drawings and description, the same is to be considered as exemplary and not restrictive in character, it being understood that only illustrative embodiments thereof have been shown and described and that all changes and modifications that come within the spirit of the disclosure are desired to be protected.

The invention claimed is:

1. An ostomy wafer comprising:
an external layer having an opening to permit the passage of effluent therethrough and a first adhesive to adhere to external skin around a stoma of an ostomate;
a convex layer coupled to the external layer that includes a stoma channel sized to at least partially receive the stoma, at least one groove radially spaced from the stoma channel that extends at least partially through the convex layer to facilitate deformation of the convex layer complementary to a shape of the stoma, and a second adhesive to further adhere to the ostomate,
wherein:
the at least one groove includes a plurality of grooves spaced circumferentially from one another about the convex layer, and
at least two of the plurality of grooves extend through the convex layer to different depths.

2. The ostomy wafer of claim 1, wherein the external layer includes a three layer tri-laminate adhesive structure.

3. The ostomy wafer of claim 1, wherein at least one of the plurality of grooves extends through the convex layer to a depth that is less than an entire height of the convex layer.

4. The ostomy wafer of claim 3, wherein at least one of the plurality of grooves extends through the convex layer to a depth that is equal to the entire height of the convex layer.

5. The ostomy wafer of claim 1, wherein the plurality of grooves are distributed over less than 10% of an entire radial area of the ostomy wafer.

6. The ostomy wafer of claim 1, wherein:
the plurality of grooves include two sets of grooves that are arranged circumferentially opposite one another about the convex layer, and
each of the two sets of grooves includes multiple grooves that extend from a proximal end to a distal end of the convex layer.

7. The ostomy wafer of claim 6, wherein the multiple grooves converge toward the distal end.

8. The ostomy wafer of claim 1, wherein the plurality of grooves include six grooves that are circumferentially distributed evenly around the convex layer.

9. The ostomy wafer of claim 8, wherein each of the six grooves extends from a proximal end toward a distal end of the convex layer.

10. The ostomy wafer of claim 9, wherein a width of each of the six grooves decreases toward the distal end.

11. An ostomy wafer comprising:
an external layer having an opening to permit the passage of effluent therethrough and a first adhesive to adhere to external skin around a stoma of an ostomate;
a convex layer coupled to the external layer that includes a stoma channel sized to at least partially receive the stoma, at least one groove radially spaced from the stoma channel that extends at least partially through the convex layer to facilitate deformation of the convex layer complementary to a shape of the stoma, and a second adhesive to further adhere to the ostomate,
wherein:
the stoma channel includes a built-in structure, and
the built-in structure is located interiorly of an internal surface of the convex layer that defines the stoma channel.

12. The ostomy wafer of claim 11, wherein the external layer includes a three layer tri-laminate adhesive structure.

13. The ostomy wafer of claim 11, wherein:
the at least one groove includes a plurality of grooves spaced circumferentially from one another about the convex layer, and
at least two of the plurality of grooves extend through the convex layer to different depths.

14. The ostomy wafer of claim 11, wherein:
the at least one groove includes a plurality of grooves spaced circumferentially from one another about the convex layer, and
at least one of the plurality of grooves extends through the convex layer to a depth that is less than an entire height of the convex layer.

15. The ostomy wafer of claim 11, wherein:
the at least one groove includes a plurality of grooves spaced circumferentially from one another about the convex layer,
at least one of the plurality of grooves extends through the convex layer to a depth that is less than an entire height of the convex layer, and
at least one of the plurality of grooves extends through the convex layer to a depth that is equal to the entire height of the convex layer.

16. An ostomy wafer comprising:
an external layer having an opening to permit the passage of effluent therethrough and a first adhesive to adhere to external skin around a stoma of an ostomate;
a convex layer coupled to the external layer that includes a stoma channel sized to at least partially receive the stoma, a plurality of grooves radially spaced from the stoma channel that extend at least partially through the convex layer to facilitate deformation of the convex layer complementary to a shape of the stoma, and a second adhesive to further adhere to the ostomate,
wherein at least one of the plurality of grooves extends through the convex layer to a depth that is equal to an entire height of the convex layer.

17. The ostomy wafer of claim 16, wherein at least one of the plurality of grooves extends through the convex layer to a depth that is less than the entire height of the convex layer.

18. The ostomy wafer of claim 16, wherein the external layer includes a three layer tri-laminate adhesive structure.

19. The ostomy wafer of claim 16, wherein:
the plurality of grooves include two sets of grooves that are arranged circumferentially opposite one another about the convex layer,
each of the two sets of grooves includes multiple grooves that extend from a proximal end to a distal end of the convex layer, and
the multiple grooves converge toward the distal end.

20. The ostomy wafer of claim 16, wherein the plurality of grooves include six grooves that are circumferentially distributed evenly around the convex layer.

* * * * *